United States Patent [19]
Doneen et al.

[11] Patent Number: 6,102,872
[45] Date of Patent: Aug. 15, 2000

[54] GLUCOSE DETECTOR AND METHOD

[75] Inventors: Byron A. Doneen, Laguna Hills, Calif.;
G. Russell Warnick, Issaquah, Wash.;
Holden H. Harris, Irvine, Calif.

[73] Assignee: Pacific Biometrics, Inc., Lake Forest, Calif.

[21] Appl. No.: 09/072,115

[22] Filed: May 4, 1998

Related U.S. Application Data

[60] Provisional application No. 60/064,067, Nov. 3, 1997.

[51] Int. Cl.[7] ......................................................... A61B 5/00
[52] U.S. Cl. .......................... 600/582; 600/365; 600/584; 422/50
[58] Field of Search ..................................... 600/345, 347, 600/349, 365, 573, 580, 582, 584; 128/898; 422/50, 56, 58, 61; 435/14

[56] References Cited

U.S. PATENT DOCUMENTS

| | | | |
|---|---|---|---|
| 3,964,871 | 6/1976 | Hochstrasser | 23/253 TP |
| 4,248,829 | 2/1981 | Kitajima et al. | 422/56 |
| 4,750,496 | 6/1988 | Reinhart et al. | 600/347 |
| 4,817,632 | 4/1989 | Schramm | 128/769 |
| 5,056,521 | 10/1991 | Parsons et al. | 128/635 |
| 5,103,836 | 4/1992 | Goldstein et al. | 128/760 |
| 5,179,288 | 1/1993 | Miffitt et al. | 250/564 |
| 5,334,502 | 8/1994 | Sangha | 435/7.21 |
| 5,335,673 | 8/1994 | Goldstein et al. | 600/573 |
| 5,714,341 | 2/1998 | Thieme et al. | 435/22 |
| 5,753,452 | 5/1998 | Smith | 435/14 |
| 5,830,410 | 11/1998 | Thieme et al. | 422/58 |
| 5,856,195 | 1/1999 | Charlton et al. | 436/50 |
| 5,871,695 | 2/1999 | Khartchenko et al. | 422/56 |

Primary Examiner—Cary O'Connor
Assistant Examiner—Charles Marmor, II
Attorney, Agent, or Firm—Knobbe, Martens, Olson & Bear, LLP

[57] ABSTRACT

A non-invasive glucose monitoring device includes a mechanism for stimulating salivary glands secretion of saliva into oral fluid prior to collecting a sample of the oral fluid. A mechanism is provided for detecting the amount of glucose in the sample, a mechanism also being provided for quantitating blood glucose level based on the amount of glucose detected. A method of non-invasively monitoring glucose includes the steps of stimulating salivary glands secretion of saliva into oral fluid, collecting a sample of the oral fluid, detecting an amount of glucose in the sample, and then quantitating the blood glucose level based on the amount of glucose detected.

20 Claims, 18 Drawing Sheets

GLUCOSE DETECTOR AND METHOD

CROSS REFERENCE TO RELATED APPLICATIONS

This application is based on Provisional Patent Application No. 60/064,067, filed Nov. 3, 1997, entitled "Glucose Detector And Method".

GOVERNMENT SUPPORT

The research carried out in connection with this invention was supported in part by a grant from the National Institutes of Health (IR43DK50500-01). The Government has certain rights in the invention.

BACKGROUND OF THE INVENTION

1. Field of the Invention

The present invention is directed to an apparatus and method for determining blood glucose content by the collection and analysis of oral fluid.

2. Description of the Related Art

The pathogenesis of diabetes originates in sustained or periodic elevations of blood glucose and glucose in tissues secondary to a deficiency in, or insensitivity to, insulin. Glucose is linked non-enzymatically to accessible reactive sites of proteins causing altered structure and function which leads in time to diseased organs. The grade of glycation depends upon glucose concentration and the amount of derivitized protein accumulated depends upon the lifetime of the individual proteins effected. Accordingly, the significance of maintaining reduced glucose concentrations is widely accepted.

Although early studies focused on Type I diabetes patients (Cohen, 1988), it is generally believed that Type II diabetes individuals and others not taking insulin would benefit from better diabetic control. Although many patients tolerate the pin prick necessary for the taking of an actual blood sample, followed by blood analysis, a bloodless, quick and convenient test using saliva can enlist Type II individuals into an effective, better diabetic control. Type I persons would also benefit to the extent that a bloodless test would reduce the number of finger sticks required. The existence of a convenient, non-invasive test can also permit prescreening of a large number of individuals using the newly promulgated 126 mg/dL criteria.

Many prior art patents discuss the analysis of glucose in various fluids, including saliva, but do not discuss the relationship of determining blood glucose from saliva levels nor do they discuss any specific devices for obtaining the same. For example, U.S. Pat. No. 3,947,328 to Friedenberg et al., issued Mar. 30, 1976, discloses a method, apparatus and test compositions for a rapid, accurate test of concentration levels of various components of body fluids, including glucose levels in saliva. An oxidizing test is utilized to determine the levels, but no relationship is disclosed relating glucose analysis in saliva to blood levels of glucose. U.S. Pat. No. 5,139,023 to Stanley et al., issued Aug. 18, 1992, discloses a method and apparatus for non-invasive blood glucose monitoring. Blood glucose is monitored non-invasively by correlation with the amount of glucose which permeates an epithelial membrane, such as skin or a mucosa membrane within the mouth. However, the Stanley patent specifically states that it is undesirable for such a sample to be contaminated by oral fluid, specifically saliva. Although the Stanley et al. patent discloses the step of taking a sample from inside the mouth, the sample taken is not a sample of oral fluid or saliva.

U.S. Pat. No. 5,056,521 to Parsons et al., issued Oct. 15, 1991, discloses an absorbent non-reactive collecting swab which is brought into contact with a favorable surface of the oral cavity. An interstitial transudate is selectively collected from the vestibule region of the oral cavity at the conjunction of the superior labal mucous membrane and the superior gingivae between the upper canine teeth. The fluid collected is then squeezed out from the swab into a monitoring instrument located off site. The patent goes into great detail to note that, although general statements are made with regard to oral fluid, the system requires that the sample be taken from the specific mucous membrane described above so that the sample is devoid of uncontrolled oral fluid that might distort the glucose level in the sample by the diluting the desired fluid (namely, interstitial transudate, column 3, lines 35–40, of the Parsons et al. patent). From this sample, glucose levels of the sample itself are determined, the specification being devoid of any teaching of how blood levels of glucose can then be obtained. Hence, the Parsons et al. patent does not disclose any method or apparatus for utilizing whole oral fluid to determine blood glucose levels and, in fact, teaches away from using the same or from diluting a sample with such oral fluid.

In view of the above, it would be desirable to develop a non-invasive means for determining blood glucose levels. It is also desirable to provide a simple means for doing so which does not require exclusion of oral fluid from a bucual cavity device.

SUMMARY OF THE INVENTION AND ADVANTAGES

In accordance with the present invention, there is provided a non-invasive glucose monitoring device including stimulation means for stimulating salivary gland secretion of saliva into oral fluid and collection means for collecting a sample of the oral fluid. Detection means, operatively connected to the collection means, detects an amount of glucose in the sample and quantitation means operatively connected to the detection means quantitates blood glucose levels based on the amount of the glucose detected.

The present invention also provides a method of monitoring blood glucose by stimulating salivary gland secretions of saliva into oral fluid, collecting a sample of the oral fluid, detecting an amount of glucose in the sample, and finally quantitating blood glucose level based on the amount of glucose detected.

DESCRIPTION OF THE DRAWINGS

Other advantages of the present invention will be readily appreciated as the same becomes better understood by reference to the following detailed description when considered in connection with the accompanying drawings wherein:

FIGS. 6A–B are graphs showing glucose standard curves in buffer or saliva indicating a comparison of selected chromogens wherein FIG. 6A shows spiked buffers and saliva and FIG. 6B shows only spiked saliva;

FIGS. 7A–B are graphs illustrating a glucose standard curve wherein FIG. 7A is a standard curve for in phosphate buffer and FIG. 7B is a standard curve and assay variation;

FIGS. 10A–B are graphs showing oral glucose contamination of saliva following ingestion, wherein FIG. 10A shows oral glucose ingestion being present and FIG. 10B are results where there was no ingestion of glucose;

FIG. 11C showing glucose collected by venipuncture vs. SalivaSac® glucose, and

FIG. 12B shows the same comparison but using all subjects, not only stimulated subjects using the SalivaSac®.

DETAILED DESCRIPTION OF THE INVENTION

Figure 1:
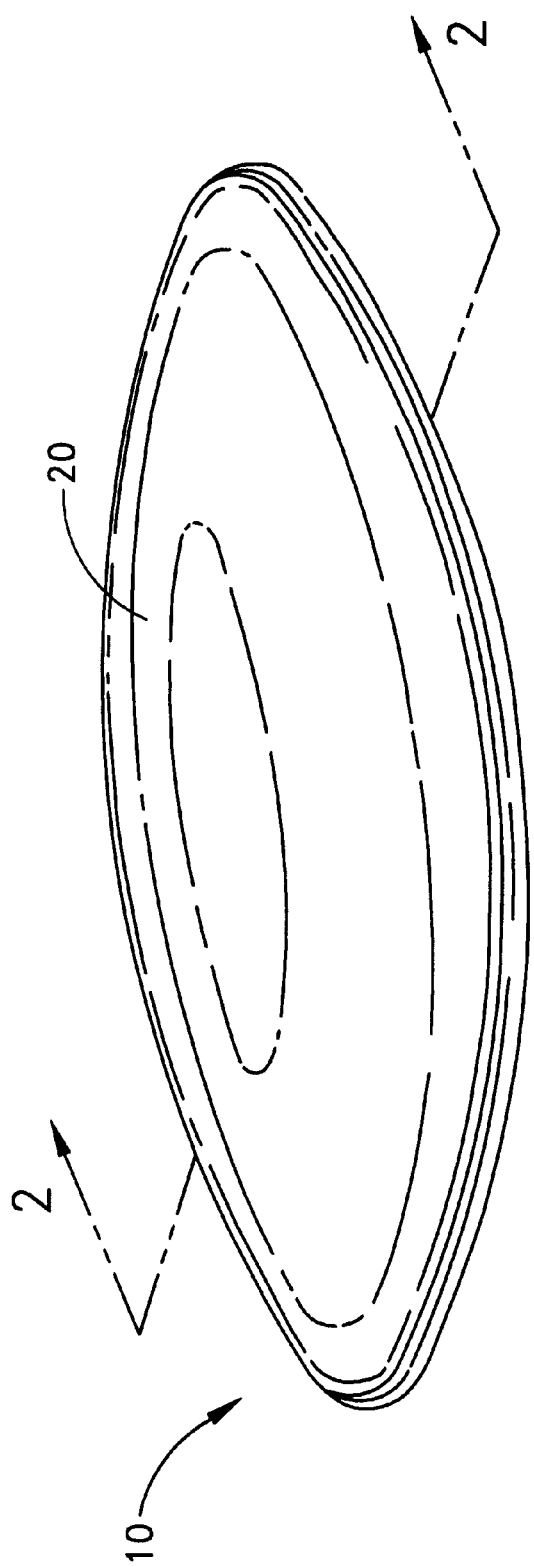
FIG. 1 is a perspective view of an oral fluid collection device made in accordance with the invention.

The present invention provides a non-invasive glucose monitoring device and method, the device including a mechanism for stimulating salivary gland secretion of saliva into oral fluid, a collection apparatus for collecting a sample of the oral fluid, a detection mechanism operatively connected to the collection device for detecting an amount of glucose in the sample, and a quantitation mechanism operatively connected to the detection mechanism for quantitating blood glucose level based on the amount of glucose detected. Thus, the elements of the present invention most generally are (1) simulation of salivation; (2) insertion of a collection device into the mouth for the period of time required for the contents to reach equilibrium with whole saliva; (3) withdrawal from the mouth of the collection device and transfer of the sample to a detection mechanism, such as a qualitative test strip as discussed below in which glucose concentration is estimated; and (4) means for calculation of estimated blood glucose. Such a system can be a integrated device wherein stimulation, collection, and quantitation are accomplished on a single strip or can be a non-integrated device, for disposal, in or out of the mouth, as discussed in greater detail below. The device is non-invasive, so it removes resistance to testing and can be used in public. It can be made inexpensively, thereby lowering economic barriers to benefits of the device. It can be a single use device and thereby avoid the spread of an infection and is also easily transportable. It is also a simple device thereby requiring little to no training for its use. Hence, the present invention, as most broadly defined, provides significant improvements over the prior art.

More specifically, the term "oral fluid" is not simply saliva, but rather the liquid contents of the mouth which include cellular secretions, components from food, saliva, as well as other components which may be secreted into the mouth, regurgitated into the mouth, or brought into the mouth by airborne means.

Oral fluid has a glucose concentration that has approximately $1/200$ to $1/100$ of the contemporaneous blood concentration. Accordingly, measurement of oral glucose can be used to estimate blood glucose.

Prior to the development of the present invention, there were few reports in the literature concluding that a general correspondence between concentration of blood and saliva glucose or whole oral fluid glucose exists. As stated above, many prior art devices excluded saliva and other oral fluid, maintaining that the inclusion of such would cause inaccuracies in glucose measurements. Borg and Berkhed (1988) demonstrated the correlation following oral loading with 75 grams of glucose. In accordance with the present invention, it is proved that Borg and Berkhed were measuring an artifact in which contamination of oral mucosa in the interval following ingestion of glucose falsely mirrored the rise in blood. Reuterving et al. (1987) measured glucose secretions of three individual salivary glands and showed that the closest correspondence with blood is in fluid from the parotid. These investigators also claimed the existence of a threshold for the spill over of the plasma glucose into the saliva of 10–15 mmL/L (180–260 mg/dL). A threshold of this type is analogous to well characterized glucose threshold of renal tubules. If this threshold identified by Reuterving et al. is accurate, then saliva cannot be used to detect glucose below about 200 mg/dL.

The data disclosed in the example section below shows that if a threshold exists, it must occur at blood concentrations substantially less than 200 mg/dL. The problem with the published work cited above is that the investigators used a standard Trinder assay, and the analytical variations seen in whole saliva, particularly at the lowest concentrations, render conclusions on detection of "zero" saliva glucose highly suspect. It is concluded based upon the present work that a new, more sensitive glucose oxidase-peroxidise chemistry in combination with the present invention makes it possible to follow saliva glucose concentrations to the lower concentrations secreted as blood declined to hypoglycemic levels. The results set forth herein show a threshold for saliva glucose to exist at least as low as 70–100 mg/dL, depending on the subject, approximately at least one half of the blood concentration specified by Reuterving et al. Based on the above, the present invention is at least useful as a diagnostic for elevated blood glucose and can certainly be predicted to be useful for lower blood glucose as well.

Figure 2:
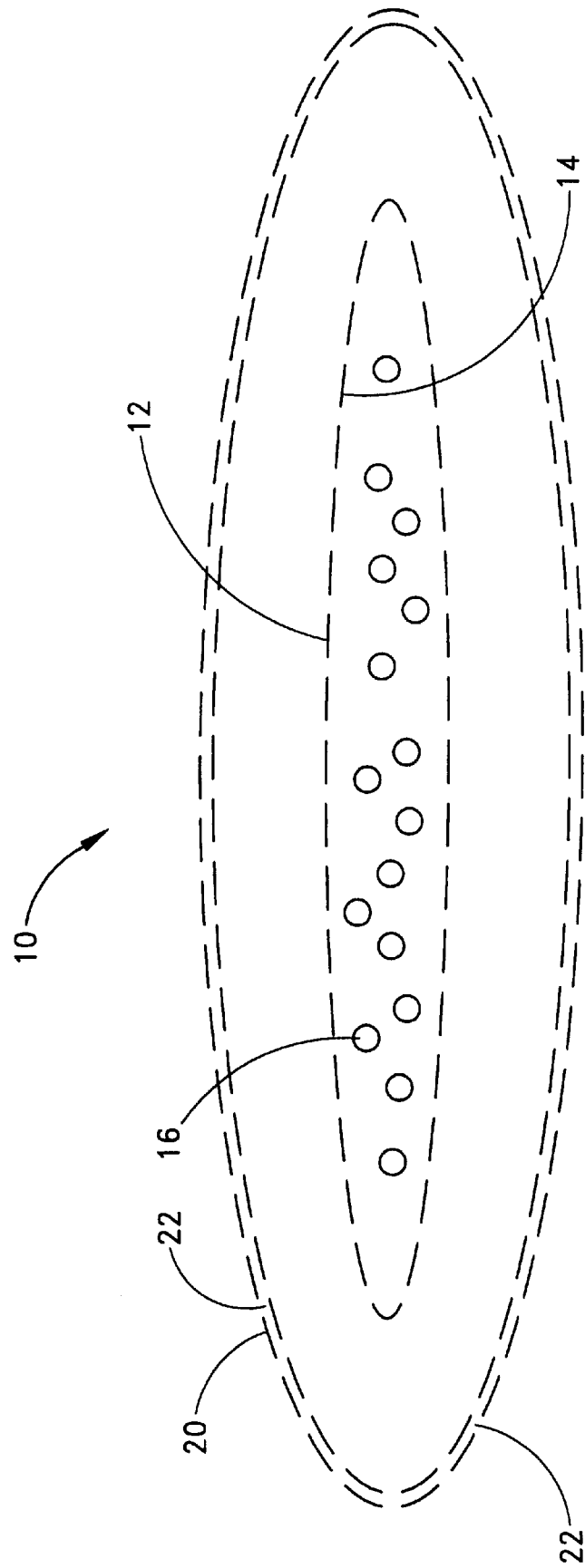
FIG. 2 is a cross-sectional view based substantially along lines 2—2 of FIG. 1.

The collection device, generally shown at 10 in FIGS. 1 and 2 is preferably an oral fluid collection article disclosed in detail in U.S. Pat. No. 4,817,632 to Schramm, issued Apr. 4, 1989, and assigned to the assignee of the present invention. The collection device is generally an ovoid small disc or pillow-shaped article adapted to fit in the mouth of a patient. The article includes a semi-permeable membrane 12 which defines an enclosed chamber 14. The chamber can include an osmotic substance 16 which is totally enclosed by the semi-permeable membrane 12.

The semi-permeable membrane 12 is made of a substance which has a plurality of pores which are of a suitable size to allow for the collection of oral fluid or which acts as a filter for filtering out unwanted particulate matter or larger molecules such as binding proteins from the sample. An example of such a membrane is Cuprophan® manufactured by Enka AG, a division of Akzo, Inc. This membrane is available as flat sheets or in a tubular form, both of which can be cut to the appropriate size. The membrane is composed of regenerated cellulose and has a nominal molecular weight cut-off of 12,000 daltons. The molecular weight cut-off, also termed the exclusion limit, is central to the function of the semi-permeable membrane. The pore size of the membrane is such that molecules larger than 12,000 daltons (such as proteins, polysaccharides and particulate matter) cannot cross the membrane 12 to enter the central chamber 14. In this way, the fluid obtained by the collection device is filtered saliva (more specifically, ultrafiltered saliva), a uniform non-viscous sample required for accurate measurement of glucose (molecular weight, 180 daltons). Any membrane, filter, fabric, paper, mineral, plastic or other material capable of allowing the passage of glucose while excluding the viscous, particulate or cellular material of oral fluid, could be used in the collection of filtered saliva. Other dialysis membranes having a range or exclusion limits could also be used, provided such membranes are permeable to glucose and allow its transport from whole saliva to the central compartment.

The osmotic substance 16 is soluble in oral fluid thereby providing an osmotic pressure inside the chamber 14 for drawing oral fluid from the mucosal cavity of the patient into the chamber 14. The membrane 12 retains at least a portion of the oral fluid in the chamber 14 for later removal, as discussed below. The osmotic substance can be a crystalline or an amorphous material which is soluble in saliva and allows interference-free analysis of the sample for whatever particular analysis is being undertaken to determine the glucose levels. Alternatively, the osmotic substance can comprise a high molarity solution of a crystalline or amorphous material which is dissolved in water or some other non-interfering solute. The osmotic substance must be non-toxic in nature and is preferably palatable.

The osmotic substance can also take the form of a stimulant of salivation. For example, the osmotic substance can be selected from the group including salts, sugars, amino acids, other organic acids and small peptides. The preferable osmotic substance is one which dissolves readily when hydrated by the moisture in oral fluid, establishes, when dissolved, an osmotic pressure capable of drawing additional fluid across the filtering surface, and is compatible with subsequent measurement of glucose in the sample obtained. For example, the osmotic substance used in collection of samples forming the data presented in FIGS. 7–12 is sodium citrate. This salt also has the effect of stimulating salivation, the first element of the present invention. A mixture of salts or other substances can also be used. An example is sodium citrate mixed with a small amount of citric acid, the latter acting to further stimulate salivation.

The basic elements of the present invention are retained if a non-osmotic material is used to collect filtered saliva. For example, absorbents or adsorbents can be used to collect saliva if they provide a method for the separation of glucose from the viscous large molecular-weight materials of whole saliva. Completely different physical forces and methods could also be used to obtain a filtered sample of oral fluid. For example, a vacuum could be created to draw oral liquid by aspiration through a filtering surface with deposition of the glucose-containing fluid in a sink. Or a positive pressure could be exerted on a saliva sample, forcing liquid through a rigid filtering surface with elaboration of filtered liquid into a central or lower compartment. One example would be a conventional filtration tube in which whole saliva is forced from an upper to a lower camber by positive pressure or by centrifugation, or by application of a negative pressure or vacuum to the lower chamber. Though the preferred embodiments illustrated in FIGS. 1–5 are based on the patent SalivaSac® with its features which allow direct insertion into the mouth, the claims of the present invention are also extended to any in-the-mouth or external device capable of producing a filtered sample of oral fluid containing a concentration of glucose equivalent to that in whole oral fluid. The expanded claims embody specifically any device or method in which expectorated saliva or oral fluid is processed further by a device external to the oral cavity which obtains an accurate measure of glucose.

Stimulation of salivation has been found to be critical. Preliminary data set forth herein is indicative that much of the controversy surrounding the correspondence between blood and saliva glucose or full oral fluid glucose can be traced to analytical imprecision associated with the sticky, viscous, and generally variable qualities of whole saliva or whole oral fluid. Testing in a limited number of subjects indicated that the blood-saliva relationship was improved by the use of the ultrafiltrate obtained by the collection device after citric acid stimulation was made in accordance with the present invention. It was felt necessary to show that the contents of the collection device accurately reflect whole saliva glucose concentration since it is whole saliva that is derived in the first instance from blood; blood glucose enters the primary secretion of salivary glands principally by paracellular diffusion through leaky epithelial cellular junctions. The rate of diffusion (and thus the amount of glucose transported per unit of time) will be increased as blood glucose rises. A minor pathway is transcellular mediated by the apocerine secretion of glandular cells (Baum, 1993). Accurate measurement of glucose in whole saliva is possible provided numerous processing steps are first employed to produce the equivalent of a filtered sample. Thus, glucose concentration in whole saliva was determined after: (1) sonication of sample at 1600 Hz (hertz); (2) freezing and thawing the sample to precipitate large molecular weight interferences; (3) centrifugation at 3000×g for 10 minutes; (4) heating the sample to 100° C.×10 minutes to eliminate glucose- and carbohydrate-hydrolyzing activities (enzymes); (5) adjusting pH to optimal assay pH (pH 6.5–7.5). This procedure produced accurate measurement of glucose to 0.06 mg/dL, as shown by quantitative recovery of glucose spiked into such samples. (It can be noted that the filtration properties of the preferred embodiment of the present invention produce a sample that is equivalent to the five-step processed whole saliva described immediately above).

The ability to measure glucose in saliva allowed for the reexamination of the time necessary for the container made in accordance with the present invention to reach equilibrium with whole saliva glucose. Subjects were observed and were found to be variable in the time to reach equilibrium, but it could require as much as 20 minutes. The more viscous and protein that enriched the saliva, the longer the time needed to reach equilibrium. Individuals with copious salvia, clear in appearance and relatively impoverished in protein often reached equilibrium at approximately the time the last of the crystalline osmotic driver in the container dissolved, six to seven minutes.

As a consequence of these results, the desirability of a dilute saliva by stimulation of salivation was recognized. The desirability of scaling down to a smaller size of the collection device was also recognized. A small device will reduce diffusion distance and destination volume and will also increase surface to volume ratio. These three factors are the principal determinants of the time required to reach equilibrium with surrounding whole oral fluid.

It was further found, as is demonstrated in the experimental section below, that stimulated saliva glucose more closely parallels blood glucose then did unstimulated saliva. This was a critical discovery. It was also found that stimulation of saliva secretion also reduced protein content of saliva and elevated sodium concentration while having a modest effect on potassium.

The conclusion from the physiological finding above is that stimulation forces saliva quickly through salivary ducts and this minimizes reabsorption of glucose, water, and sodium ions by salivary gland ductal transport systems. Therefore, stimulated saliva more nearly reflects the composition of the primary filtrate-secretion elaborated by the secretory portion of the salivary glands and it is this fluid that is derived by passive diffusion from blood. Accordingly, as described above, it is preferred to provide a stimulatory component. This is preferably accomplished, as stated above by stimulatory component being disposed within the container 10 for release therefrom. As also stated above, the preferred stimulant is citric acid.

Referring again to FIG. 2, the semi-permeable membrane 12 may be enclosed by an outer protective membrane 20 which includes macroscopic pores and is disposed about and completely exposes the membrane 12. The outer protective membrane 20 can be made of any material which would be generally pliable, tasteless, and non-toxic. Preferably, silicon materials or other materials are selected which have substantial mechanical strength to protect the inner membrane from damage due to biting by a patient and similar hazards which may be associated with the use of the present invention in a patient's mouth. The outer membrane can be made from many materials whereby saliva can pass through easily, the material having microscopic pores 22. Alternatively, the present invention can include a container 10 as described above without the use of the outer membrane 20, wherein the inner membrane 12 is made of material of sufficient mechanical strength to survive in the environment of the mouth of a patient.

Figure 3:
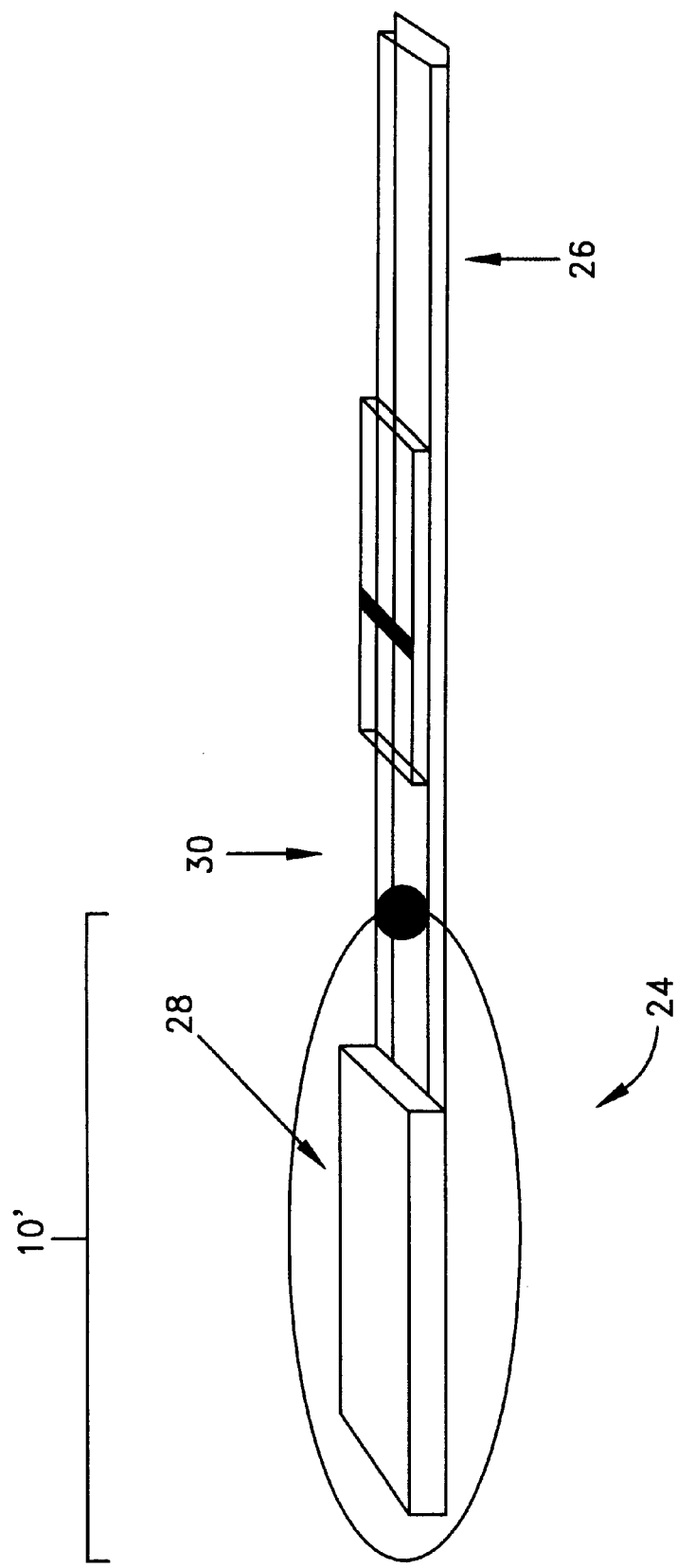
FIG. 3 is a perspective view of a second embodiment of the invention.
Figure 4:
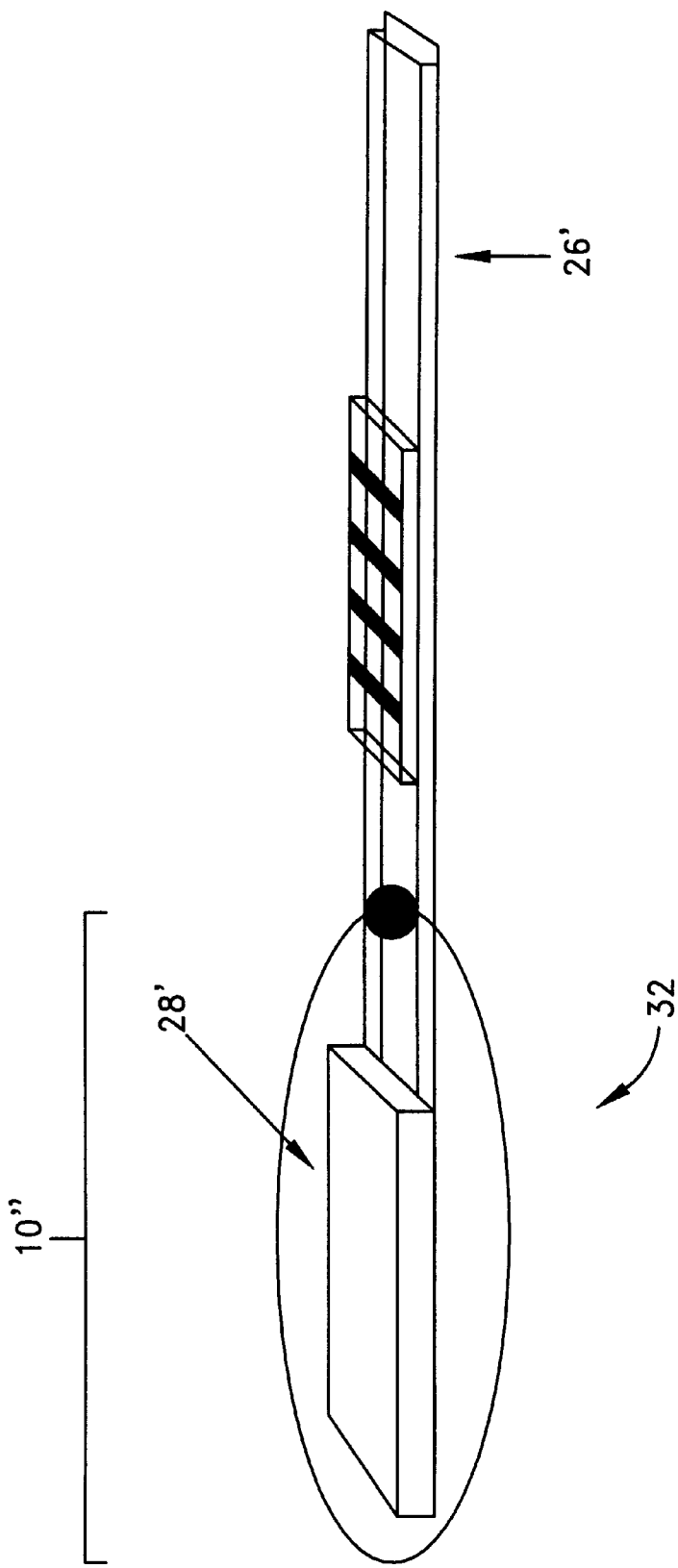
FIG. 4 is a perspective view of a third embodiment of the invention.

A preferred embodiment of the subject invention is shown in FIGS. 3 and 4. A device 24 is in the form of a test strip including a support 26. A membrane sac 10', having a structure as described above, is mounted over one end of the support 26 and contains an absorptive matrix 28. Absorptive matrix 28 can include the stimulator of salivary gland secretion, such as sodium citrate. The absorbent matrix 28 is in fluid communication by abutment with a threshold-type indicator film 30.

The film contains the enzymes glucose oxidase and horseradish peroxidase (or some other peroxidase) and a combination of dyes and accessory reagents, such as buffers and stabilizers, which are capable of producing a colored spot or line in which color intensity is proportional to the amount of glucose in the sample. Glucose oxidase applied as a dry reagent to the strip hydrolyzes sample glucose to gluconic acid with production of hydrogen peroxide The peroxidase converts the peroxide product to water and uses the electrons produced to react with the dyes to form a colored compound. The color intensity, as noted, is scaled to the amount of glucose initially present in the sample. Numerous enzyme-based glucose-sensitive strips of the general type described exist. Various dyes have been used to generate the final color product. Some of these are described in the experimental section herein.

The present invention includes any type of solid-phase strip chemistry capable of determining glucose at the concentration existing in filtered saliva or oral fluid. Moreover, as the essential elements of this invention are the use of a filtered and stimulated saliva, any method of glucose measurement could be associated with the processed sample. These include, but are not limited to, other enzyme-based system (e.g., using hexokinase or glucose dehydregenase or any glucose metabolizing enzyme), chemistry-based systems (e.g., a specific glucose reagent producing some quantifiable signal), and glucose sensors (e.g., glucose-specific electrochemistry).

Utilizing this embodiment of the invention, oral fluid is collected within the container 10' by the absorbent matrix 28. Upon contact with the oral fluid, sodium citrate is dissolved and released through the container 10' thereby stimulating saliva secretion. The collected oral fluid is retained in the matrix 28 for the period required for contents to reach equilibrium with whole oral fluid glucose. In a small collection device, this time may be two or fewer minutes. The contents of the sac are then exposed to one end of the colorimetric glucose strip. The mechanism retaining the filtered liquid can be a simple pressure-sensitive opening (port), or the rate-of-flow of sample along the test strip can be made sufficiently slow to ensure that sample has reached glucose equilibrium.

Figure 5:
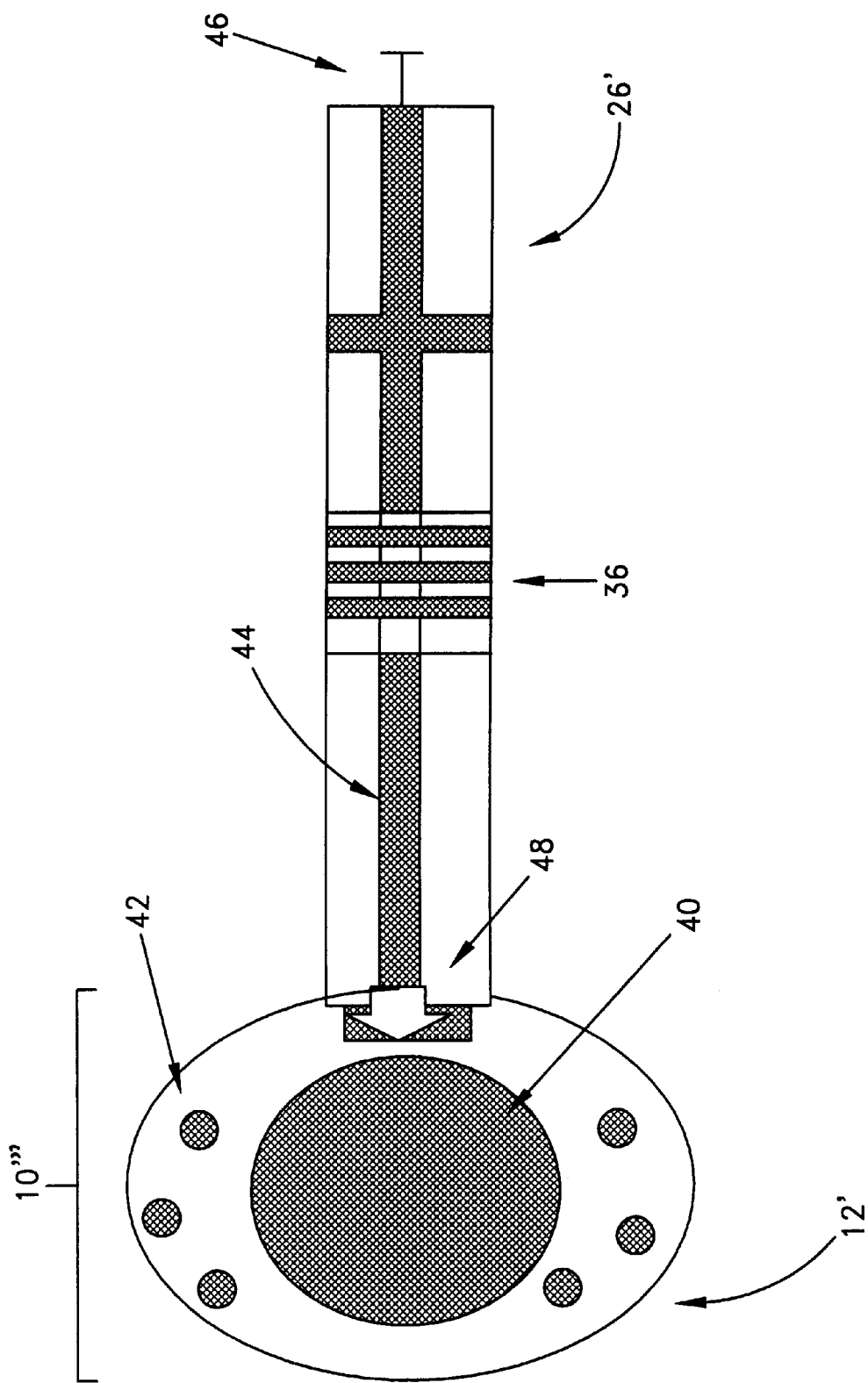
FIG. 5 is a schematic plan view of a fourth embodiment of the present invention.

An alternative embodiment of the present invention is generally shown at 32 in FIG. 4. A support strip 26', which can be similar to that shown in FIG. 3 supports a collection container 10" as described below. The collection container, containing the absorbent matrix 28' which can also contain the sodium citrate, is mounted adjacent a wicking material in communication with a thermometer-type indicator film. A thermometer type film is one in which the enzymes and dyes required to produce the colorimetric signal are arrayed from proximal to distal on the test section of the strip. As sample moves through the test zone, glucose is depleted and colored products are formed. When glucose is exhausted from the sample, no further color development can occur in the distal enzyme field. The amount of glucose in the sample is thus proportional to the linear distance of color development. A thermometer-type strip requires that an accurately measured fixed volume of sample be applied to the strip. This can be achieved in this embodiment by creation of a saturable strip having a limited (and fixed) capacity for liquid absorption, by timing the reaction to allow a known volume of sample to enter the test zone, or by application of a known sample volume obtained by a chamber of defined volume between sample and strip. The flow of liquid and its glucose up the strip proceeds by capillarity according to well known principles. The strip may contain accessory elements, such as sample volume adequacy indicators, as shown in FIG. 5, additional filtration materials, and test sections to check quality of reagents.

The indicator film can be graded to provide an indication of blood glucose level correlated from the glucose content of the collected oral fluid. Thus, the film 36 provides a detection mechanism, as well as a quantitation mechanism. Alternatively a container 10, 10' or 10", mounted on a strip 26, 26' or independent thereof shown in FIGS. 1 and 2, can be transferred to a detection device known in the art for glucose analysis. A glucose level can then be correlated to blood glucose levels.

One such embodiment would require placing the strip into a reflectance spectrophotometer similar to those currently used in monitoring blood glucose. The strip could be moved to the monitor after the sample is introduced onto the strip, or a small integrated monitor could be created to present a combined replaceable strip-plus-collection device into the mouth or sample receptacle (for the embodiment using a device external to the mouth to process the saliva sample).

The correlation with blood is obtained by solving an equation which relates blood glucose to oral fluid glucose concentration. For example, solving the linear equations shown in FIGS. 11 and 12 for "x", will produce the blood glucose concentration when the oral fluid glucose (y) is known. The exact quantitative values of the constants in this equation have not yet been determined. The nature of these constants could take one of two forms: (1) if most individuals show the same saliva to blood glucose ratios, a single equation can be developed for the subject populations; (2) or if individuals show different ratios, then each individual will be required to calibrate the saliva test against periodic measurements of their own blood glucose. In each situation, a simple equation is produced. It is understood that in actual use, the solution to the equation may be translated into an easily readable table or color chart. In the embodiment in which the collection device and strip test are incorporated into a reflectance spectrophotometer, the computation of the blood glucose concentration can be achieved by insertion of a dedicated computational chip into the monitor. These electronics thus convert a spectrophotometric signal into an estimated blood glucose value.

The preferred embodiment of the present invention is shown schematically in FIG. 5. Again, the container 10''' includes an osmotic component 40 contained within an inner membrane 12' and a citric acid component 42. The container 10''' is mounted at the end of a wicking material 34 supporting a plunger 46 containing a needle 48 therein. The needle can be used to puncture the outer and inner membranes 12', to release the collected oral fluid therefrom onto the wicking material 44. The fluid wicks across the material 44 to the indicator portion. This embodiment allows for a retention of the sample in the central compartment until the user elects to admit the sample to the strip. Thus, the voluntary act of breaking a seal or barrier is required. This embodiment would be used if it takes an unusually long time for the collection device to reach glucose equilibrium in some subjects, or if the subject prefers to analyze the sample at a later time. Therefore, the device contains a membrane-osmotic driver collection component, a dispenser of citric acid, a mount for attachment of the disposable cross-strip, and a mechanism in the form of a pin or, alternatively, a pressure-sensitive valve, to penetrate or open the container to allow a measured volume of sample of oral fluid to be transferred to the test strip. Alternatively, as shown in the various embodiments, wicking materials can be used as a means for transferring an adequate sample as indicated by an adjacent indicator on the strip.

The following experimentation demonstrates the usefulness of the present invention.

EXPERIMENT I

As observed by Borg and Birkhed (1988), saliva glucose in whole oral fluid rose and fell in concert with blood glucose from a finger stick following an ingestion of bollus glucose (25, 50, and 75 g) in non-diabetic volunteers. However, utilizing the present invention, duplication was achieved of the oral elevation by having subjects dissolve glucose tablets in the mouth, followed by expectoration without swallowing. In this experiment, there was no, or at least only minor, elevations in blood glucose. It can be concluded that following absorption of glucose by oral mucosea, tissue becomes a dominant source or sink of salivary glucose. It can take two hours for saliva glucose to reach precontamination baseline values. Various rinsing protocols using water, concentrated sodium chloride, and glucose-free astringent mouthwashes only modestly reduced the time to baseline. It was also determined that routine meals not regulated for content have the same effect as glucose tablets, though the degree of oral contamination was reduced compared with tablets or concentrated liquid glucose.

EXPERIMENT II

It was previously hypothesized that saliva glucose could be detected even in periods of hypoglycemia given the development of a highly sensitive glucose assay. When such an assay was perfected, it was used to confirm the existence saliva glucose threshold, though at about one-half the blood glucose concentration claimed by Reuterving et al. (1987). The confirmation of the threshold of 70 to 100 mg/dL in eight non-diabetic subjects led to the investigation of saliva glucose levels in normal to hyperglycemic persons. A study in 18 diabetic subjects was initiated, the subjects being screened by finger stick to ensure the existence of the study criteria of greater than 250 mg/dL. Subjects contributed whole saliva samples and samples collected by a device made in accordance with the present invention. Subjects also provided venipuncture blood for measurement of glucose by the reference method. This method uses the enzyme hexokinase to phosphorylate (using ATP) glucose to glucose-6-phosphate. Glucose-6-phosphate is next converted to 6-phosphogluconate with reduction of $NADP^+$ to NADPH, the latter reaction read with a spectrophotometer (340 nm) after a specified period of time; the amount of NADPH produced is proportional to the amount of glucose in the deproteinized sample.

The data reveal a correspondence between finger prick blood glucose and glucose derived by the device made in accordance with the present invention when blood and saliva samples are taken at the same time. The correspondence with venipuncture glucose is also high, shown in FIG. 12.

EXPERIMENT III

A highly sensitive assay for saliva glucose was derived. Table 1 lists most visible wavelength chromogens investigated, identifies the limits of glucose detection (+2 standard deviations of blank in phosphate buffer), and tabulates time to complete assay (high standard OD 1.2–1.8). These assays were done in solution (96 well plate, sample volume 100 μL) at 37° C. with samples added last.

TABLE 1

Visible Wavelength Chromogens in GO/HRP Glucose Assays Investigated

|  | Sensitivity mg/dL | Response OD/mg/dL | Time to Completion minutes at 37° |
|---|---|---|---|
| *Coupled Reagents: | | | |
| MBTH-- | | | |
| DMAB | 0.04 | 0.18 | 15 |
| CTA | 0.06 | 0.13 | 20 |
| 3,6 CTA | 0.12 | 0.08 | >30 |
| 5,7 CTA | 0.17 | 0.12 | 25 |
| 4-AA-- | | | |
| 4-HBS | 0.16 | 0.14 | 15 |
| *Single Reagents: | | | |
| O-Di | 0.29 | 0.04 | >30 |
| OPD | 0.16 | 0.08 | not done |
| 5-AS | 0.25 | 0.02 | >30 |

TABLE 1-continued

Visible Wavelength Chromogens in GO/HRP Glucose Assays Investigated

|      | Sensitivity mg/dL | Response OD/mg/dL | Time to Completion minutes at 37° |
|------|-------------------|-------------------|-----------------------------------|
| ABTS | 0.15              | 0.08              | 15                                |
| TMB  | 0.22              | 0.11              | 20                                |

*Names of compounds used in Appendix I. Assays done in phosphate or Tris buffers.

Figure 6A:
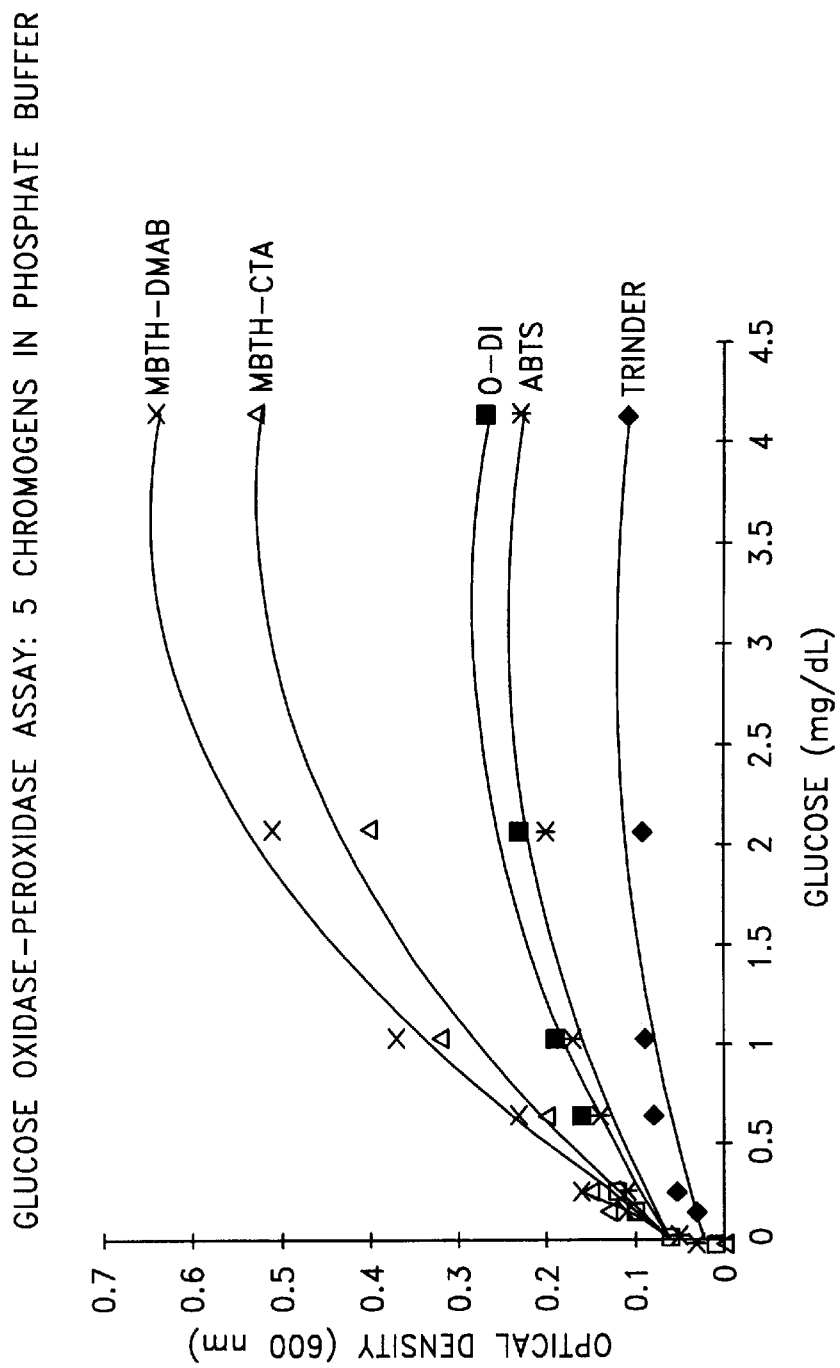
Figure 6B:
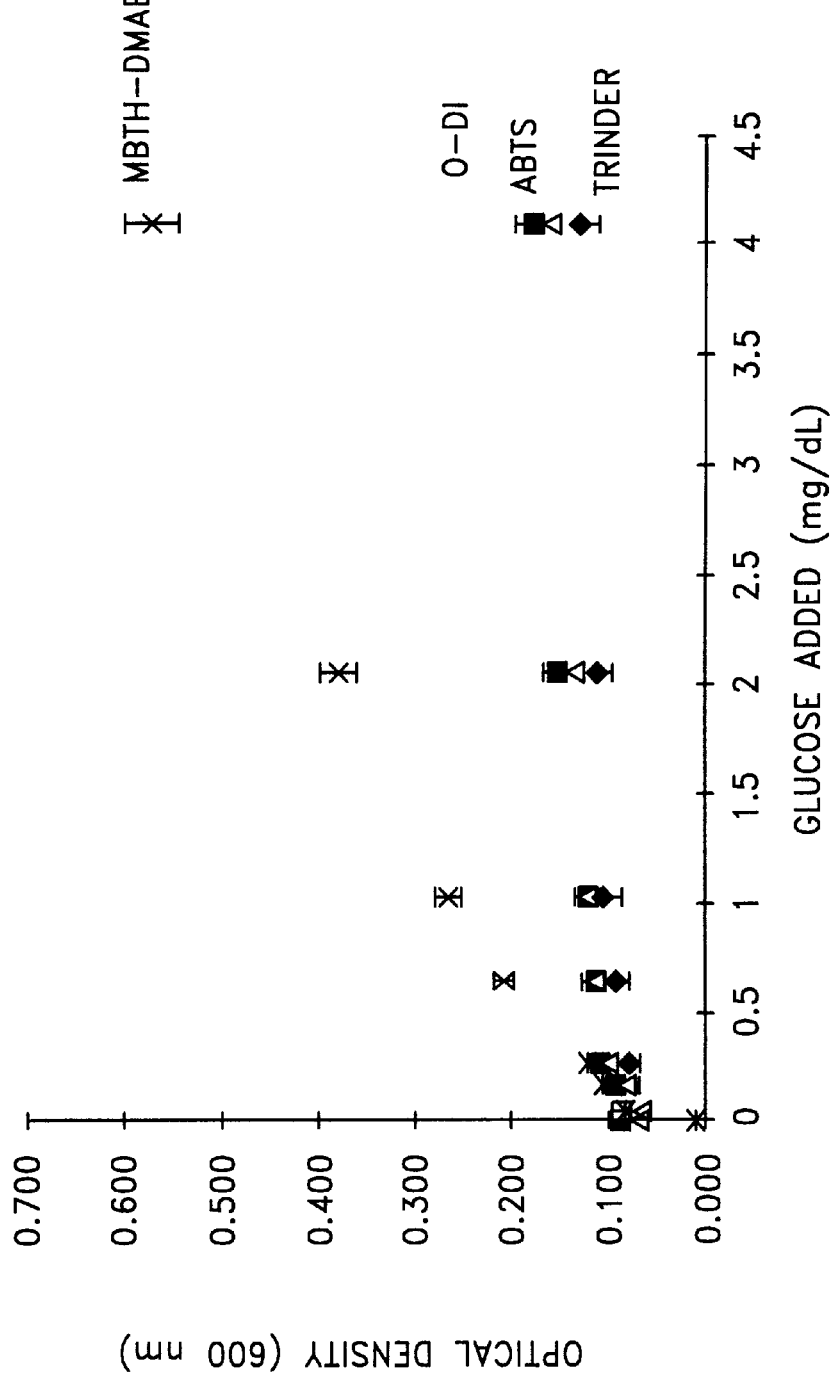

FIG. 6A summarizes a subset of the visible chromogens used with glucose oxidase-peroxidase in development of a more sensitive glucose assay. Glucose was spiked into two different matrices: 20 mM phosphate buffer (pH 7.0), and whole saliva processed as described above but without heating to 100°×10 min (saliva pH, 6.9). The whole saliva used was donated by a single fasting individual and did not have detectable glucose before spiking in any of the assays. The MBTH system, compared to other chromogens, showed the greatest sensitivity and steepness of response with acceptable linearity in the target dynamic range. FIG. 6B emphasizes the performance of various systems in saliva and shows that the MBTH (in this case, with CTA) system is superior to others (and also that it behaves in saliva as in buffer, with the exception that the limit of detection is slightly higher).

Figure 7A:
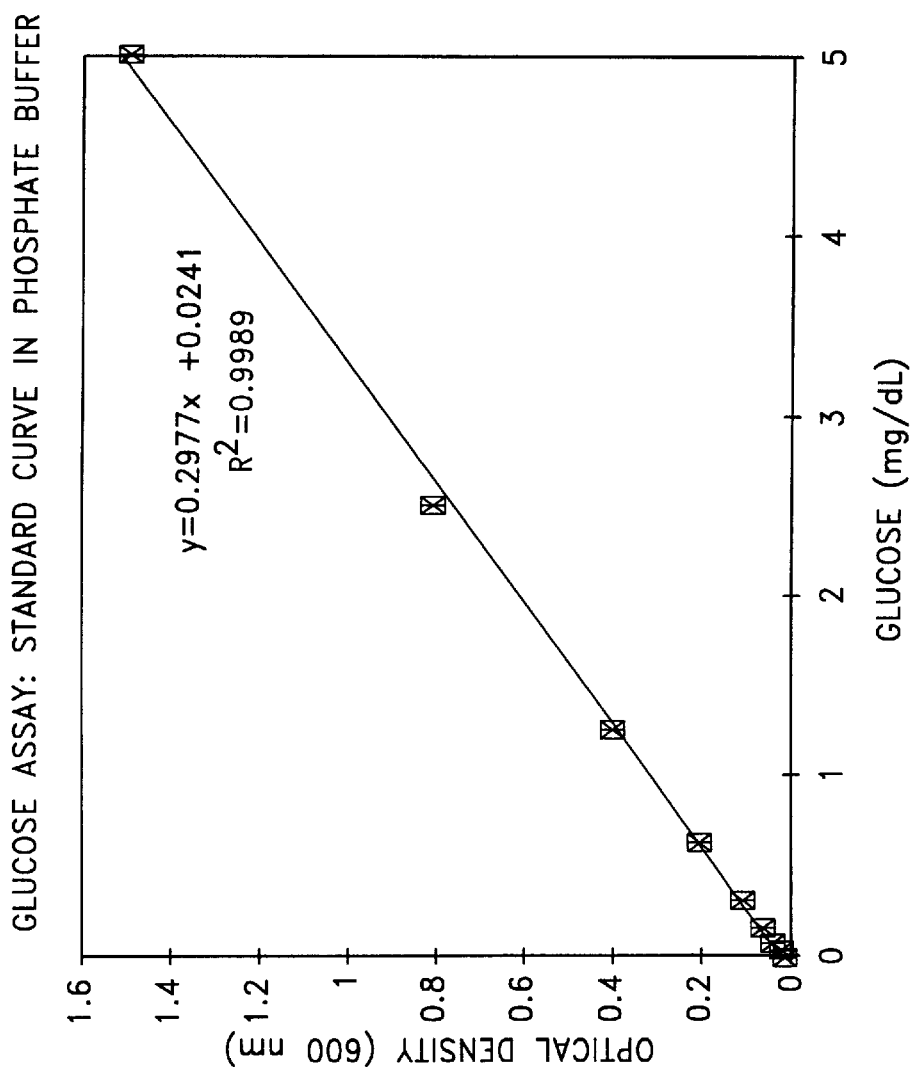
Figure 7B:
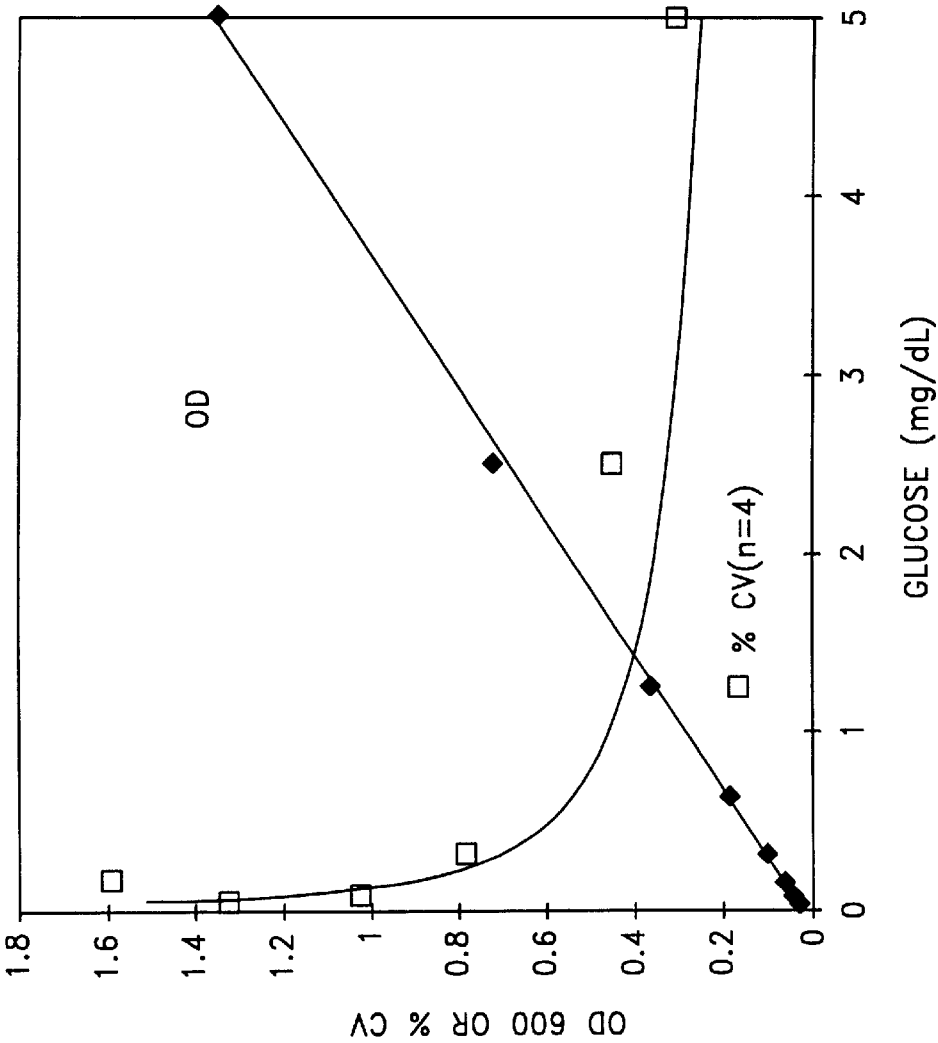

FIG. 7 shows the results in the final modification made to the MBTH assay; this was in linking color generation to reduction of MBTH and DMAB. This assay could detect 0.04 mg/dL glucose at the two standard deviations criterion (0.06 mg/dL in saliva). The percent coefficient of variation was less than 2% below 1 mg/dL and less than 0.6% when glucose exceeded 1 mg/dL (FIG. 7B). Table 2 summarizes composition and methods used for the GO/HRP-MBTH/DMAB glucose assay in the remaining studies shown.

TABLE 2

Composition of GO/MBTH Glucose Assay

| Solution | Enzyme                        | Chromogen         | Buffer                |
|----------|-------------------------------|-------------------|-----------------------|
| 1        | Horseradish Peroxidase 12.5 U/mL | DMAB* 30 mM      | 100 mM PO4 pH 7.5     |
| 2        | Glucose Oxidase 37.5 U/mL     | MBTH** 1.5 mM     | 100 mM PO4            |

100 μL sample; 20 μL Solution 1; 20 μL Solution 2; Incubate 15 min at 37° or 25 min at room temperature. Read OD @ 600 nm.
*3-dimethylaminobenzoic acid
**3-methyl-2-benzo-thiazolinone hydrazone (dissolved in methanol at 15 mM)

EXPERIMENT IV

A series of experiments was performed to learn if whole saliva could be processed in a manner that would reduce variability and improve accuracy in assay of glucose. As summarized above, it was determined that both goals could be achieved only after treatment of saliva using four separate procedures: sonication, mucoprotein precipitation using freeze-thawing, precipitation of soluble proteins using 10% TCA (trichloracetic acid), and heating processed saliva to 100° C. for 10 minutes. In most cases, each step requires its own subset of manipulations, such as centrifugation or readustment of pH to assay optimum.

Table 3 shows one experiment in which one sample of whole (unstimulated) saliva was processed according to the sequence outlined. Separate aliquots were spiked with glucose at 1.5 mg/dL or 0.1 mg/dL before sample treatment, and processed in parallel. After each processing step, the product was assayed using the MBTH/DMAB glucose assay. The % CV for each assay (4 replicates A) is shown in parentheses to indicate variability.

TABLE 3

Effect of Processing Whole Saliva on Accuracy of Glucose Assay

| Sample      | 0 mg/dL Spike | (% CV) | 1.5 mg/dL | (% CV) | 0.1 mg/dL | (% CV) |
|-------------|---------------|--------|-----------|--------|-----------|--------|
| Whole       | 1.71          | (18.3) | 3.63      | (28.1) | 1.92      | (25.0) |
| Sonicated   | 1.94          | (20.4) | 2.79      | (16.3) | 1.37      | (14.6) |
| Freeze-Thaw | 0.75          | (10.6) | 1.48      | (12.9) | 0.86      | (13.5) |
| TCA Ppt     | 0.64          | (5.6)  | 1.63      | (8.2)  | 0.68      | (11.5) |
| Heat 100°   | 0.62          | (5.8)  | 1.77      | (7.3)  | 0.70      | (9.9)  |
| % Expected in Final Step: |  |        | 83.5%     |        | 97.2%     |        |

Figure 8:
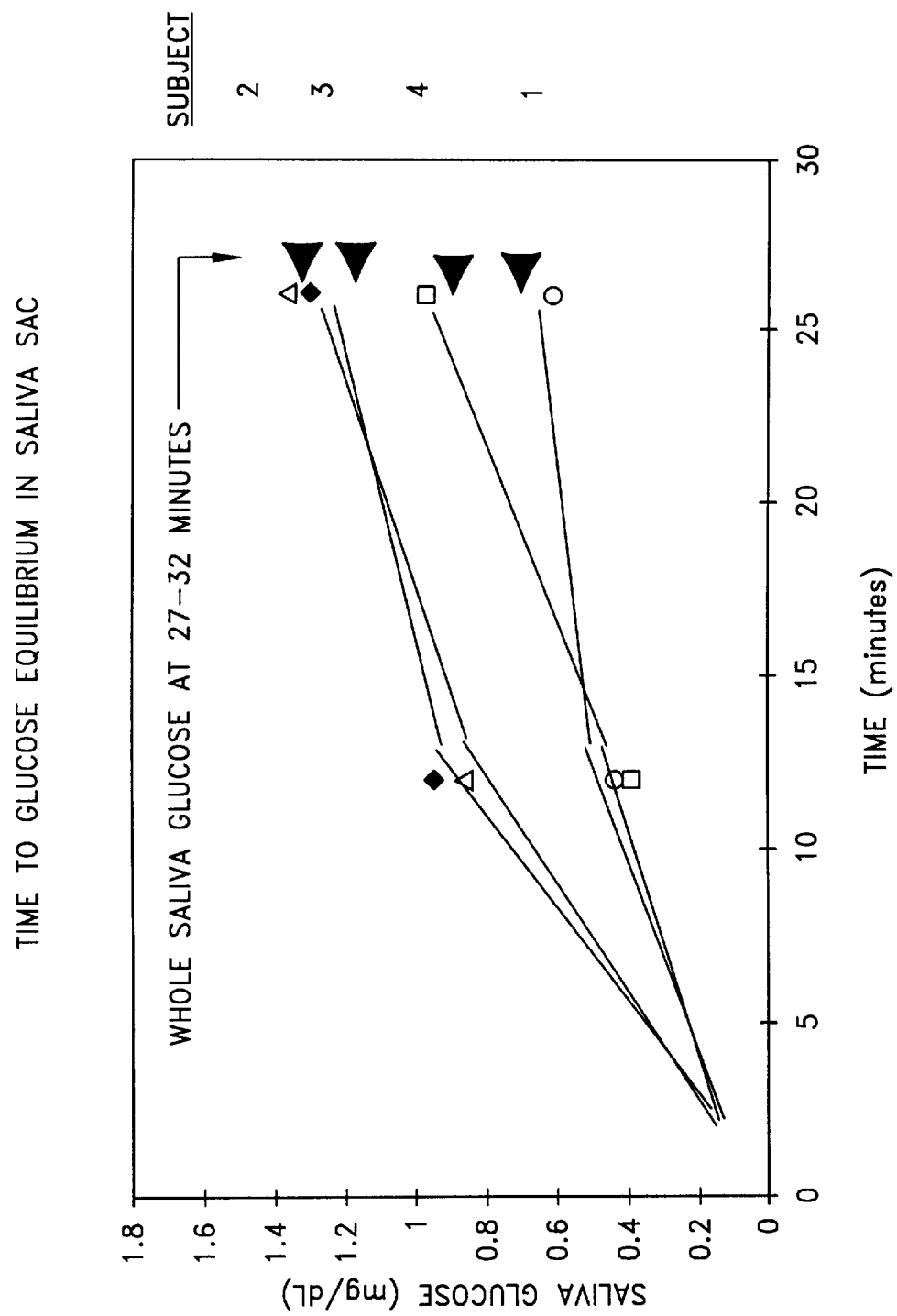
FIG. 8 is a graph showing the time to saliva glucose equilibrium in the subject invention.

Spiked glucose was measured in saliva with approximately 80–110% recovery. However, the saliva of individuals is quite different with less viscous samples being less variable and requiring less processing. Capacity of the present invention to obtain a sample which accurately reflects, at equilibrium, whole saliva glucose was examined. One such experiment is shown in FIG. 8. In these four nondiabetic subjects, glucose collected and measured in accordance with the present invention reached approximately (±12%) the whole saliva concentration in 26 minutes (each subject placed two devices in the mouth and these were removed at 12 minutes and 26 minutes: The arrowheads on the right indicate the glucose concentration measured in whole saliva collected between minutes 26–29). These results showed that the contents collected did equal concentration in whole saliva, though the time required was somewhat longer than the earlier estimate. The longest times required seemed to be in those individuals with the thickest whole saliva.

Subsequently, it became possible to obtain a less viscous saliva in all subjects by stimulation with citric acid. With citric acid, time to reach equilibrium with whole saliva glucose appeared to be reduced to 12 minutes.

Table 4 illustrates an experiment of the type described above in which three nondiabetic subjects and one diabetic subjects had two devices, made in accordance with the present invention placed in the mouth, but on this occasion, following the citric acid. When compared to whole saliva (collected after removal of the last device and reapplication of citric acid), most subjects showed glucose values from fluid collected by the subject device approximately equal to whole saliva by 12 minutes, but at least one required longer.

TABLE 4

Time to Reach the Equilibrium Glucose Concentration in a Device Made in Accordance with the Present Invention Following Citric Acid Stimulation of Salivation

| Subject | Time (minutes) | SalivaSac Glucose (mg/dL) | End Whole Saliva Glucose (mg/dL) |
|---------|----------------|---------------------------|----------------------------------|
| 1       | 12             | 0.85                      | 0.94                             |
|         | 20             | 0.88                      |                                  |
| 2       | 12             | 1.14                      | 1.43                             |
|         | 20             | 1.56                      |                                  |
| 3       | 12             | 0.43                      | 0.52                             |
|         | 20             | 0.57                      |                                  |

TABLE 4-continued

Time to Reach the Equilibrium Glucose Concentration
in a Device Made in Accordance with the Present
Invention Following Citric Acid Stimulation of Salivation

| Subject | Time (minutes) | SalivaSac Glucose (mg/dL) | End Whole Saliva Glucose (mg/dL) |
|---|---|---|---|
| 4* | 12 | 3.27 | 3.67 |
|  | 20 | 3.35 |  |

Values are means of replicate determinations with Standard Errors less than 7.3% (SalivaSac) or 11.8% (whole saliva) of the mean.
*Diabetic subject.

Stimulation of salivation promotes collection of a filtered sample, collected in accordance with the present invention, which reflects whole saliva glucose in less time than in unstimulated saliva. This advantage apparently originates from reduced viscosity which will increase diffusability of glucose. The deficiency in the large molecular weights mucopolysaccharides and mucoid proteins in stimulated saliva may also prevent "coating" of the sac membrane which could also interfere with flux of analyte.

Subsequent investigation unexpectedly showed that glucose in stimulated saliva (whole processed saliva or when collected by the present invention) also showed closer parallelism with blood glucose than did unstimulated saliva. Some explanation for this improved correspondence was gained by examination of certain biochemical properties of saliva which relate to mechanisms of secretion. In particular, it was investigated as to whether glucose absorption from the primary filtrate by salivary ducts might be minimized when flow through the ducts was maximized by stimulation. It was inferred that this is the case from the data presented in Table 5. It compares mean content of glucose, Na+, K+, soluble protein and total protein (and polysaccharides) in five individuals who contributed whole unstimulated and stimulated saliva within a 20 minute period. Soluble protein was measured using the Pyrogallol assay; the insoluble material was measured as dry weight of the freeze-thaw pellet.

TABLE 5

Concentrations of Protein, Sodium, Potassium and Glucose in Citric Acid Stimulated and Unstimulated Whole Saliva

|  | Insoluble Protein (mg/mL) | Soluble Protein (mg/mL) | Na+ (mM) | K+ (mM) | Glucose (mg/dL) |
|---|---|---|---|---|---|
| Unstimulated | 7.5 ± 1.2 | 0.4 ± 0.2 | 10.4 ± 2.9 | 5.7 ± 1.9 | 0.6 ± 0.4 |
| Stimulated | 3.3 ± 0.9* | 0.5 ± 0.1 | 37.2 ± 5.9* | 8.8 ± 2.5 | 1.3 ± 0.5* |

Values are means ± SEM; n = 5.
*p ≤ 0.05, t-test.

Increased glucose concentration in stimulated saliva is consistent with reduced net reabsorption by the ducts. Likewise, the elevation in Na+ results from reduced time of exposure to ducted Nc+ pump (Na-K-ATPase; 9). Stimulation of flow rate through the ducts would reduce net effect of any reabsorptive systems. The reality of a glucose reabsorptive system is also supported by existence of the saliva glucose threshold; the reduced amount of glucose diffusing from plasma when its concentration is low can apparently be completely cleared by the duct, provided flow rate is sufficiently slow.

Interestingly, the concentration of soluble protein is not significantly effected by stimulation, whereas insoluble materials are reduced. The reduced components are in the viscous, sticky material normally precipitated (in our method) by freeze-thawing and centrifugation. Its lower content can be observed in the "watery" saliva elaborated immediately upon stimulation. Soluble protein (to the extent it can be discussed as single class) is not lowered by stimulation; apparently secretion of some macromolecules is matched to the volume discharged, and others (especially the larger moieties) are not.

There is no ready explanation for the elevation in K+ upon stimulation. (3). It seems reasonable that with a reduction in reabsorption, saliva glucose will more precisely reflect the concentration of glucose deposited in the primary filtrate of salivary secretions. And this concentration will, in turn, be set by the free glucose concentration in plasma from which saliva glucose is ultimately derived.

The performance of the GO-HRO-MBTH/DMAB assay in the device of the present invention matrix following the dissolution of the $Na_3$Citrate osmotic drives was next examined. The focus was in the pH of this medium and the possible consequences of the elevated sodium ion and citrate concentrations. As sodium citrate is a weak base, it was found that in most subjects, pH in the device varied between 6.9 and 8.2. This is an important finding because the pH of the stimulated whole saliva is typically between 2 and 4, an effect of the acidic stimulant. Thus, $Na_3$Citrate in the Sac and citric acid in the stimulant are acting as the conjugate pairs of a buffer, the effect in the Sac producing a pH in the optimal range of the enzyme assay.

Figure 9:
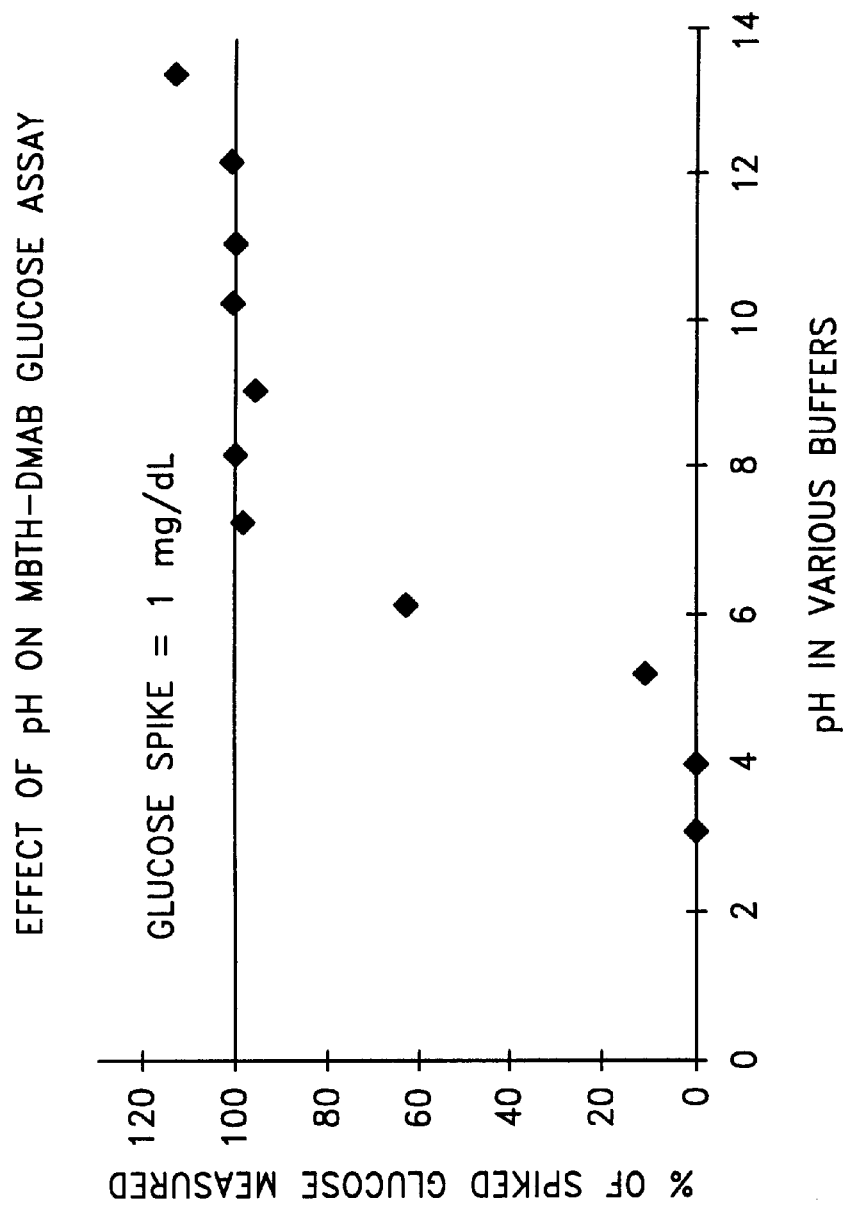
FIG. 9 is a graph showing the effect of pH on the glucose assay.

FIG. 9 shows the effect of pH on the Vmax of the assay when it is performed in 500 mM Na3Citrate. The concentration of osmotic driver was arrived at by measuring Na+ concentration (flame photometry) in several samples after the equilibration period of 20 minutes in the mouth. Na+ concentration was approximately 1.5 M(range, 1.25–1.8 mM) and the citrate concentrations was computed assuming that the ratio of Na/Citrate was maintained at 3. Conditions prevailing in the sample collected by the present invention are compatible with sensitive and accurate performance of the solution version of the strip assay.

Earlier research centered on development of a new sensitive glucose assay and in defining conditions in whole saliva and in samples obtained by the present invention that permitted accurate quantitation of saliva glucose. In the remaining results shown, the assay was used in human subjects to establish the basic feasibility of a saliva test as a potential substitute for blood tests.

EXPERIMENT V
Factors Influencing Diagnostic Specificity of Saliva

Figure 10A:
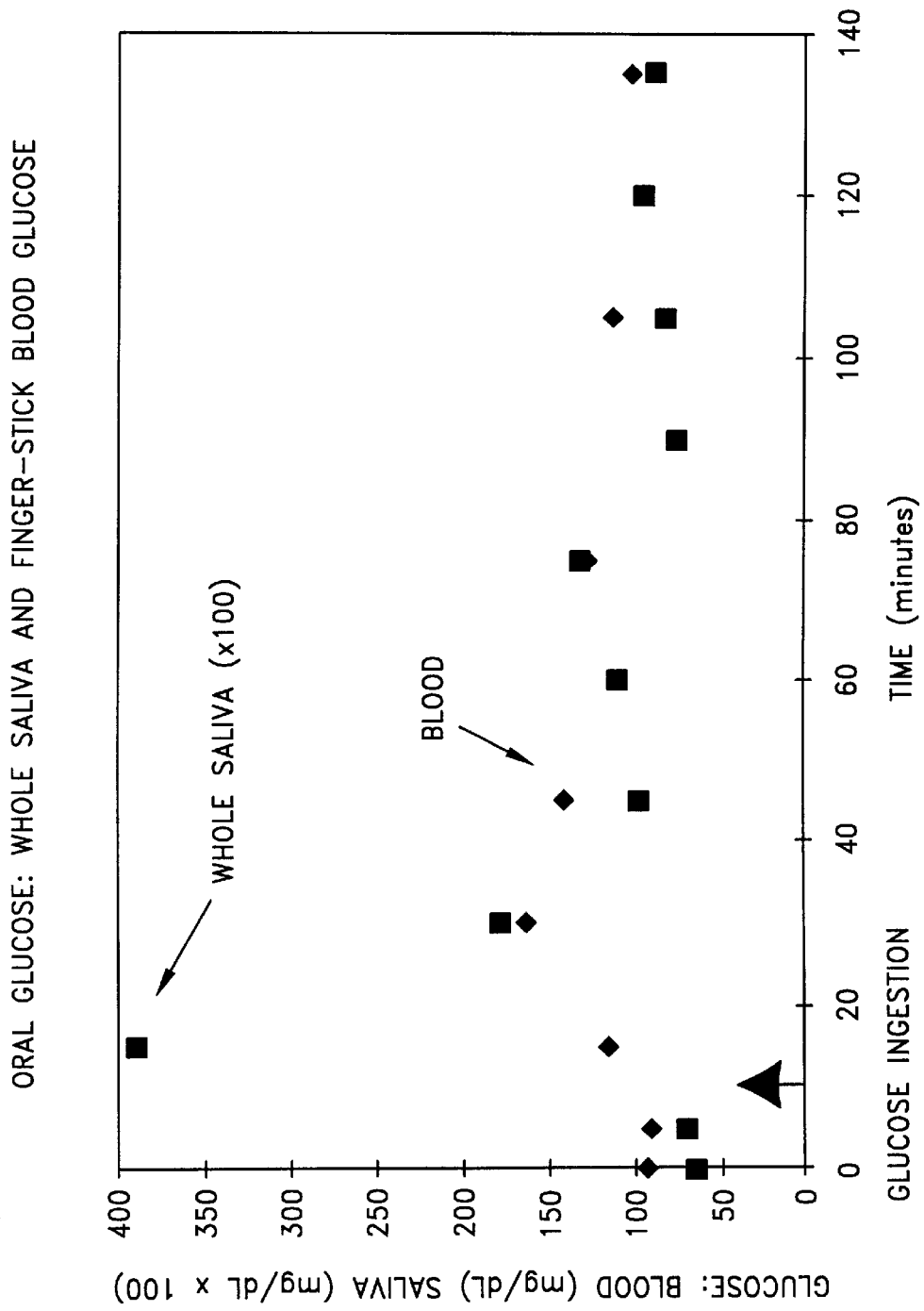
Figure 10B:
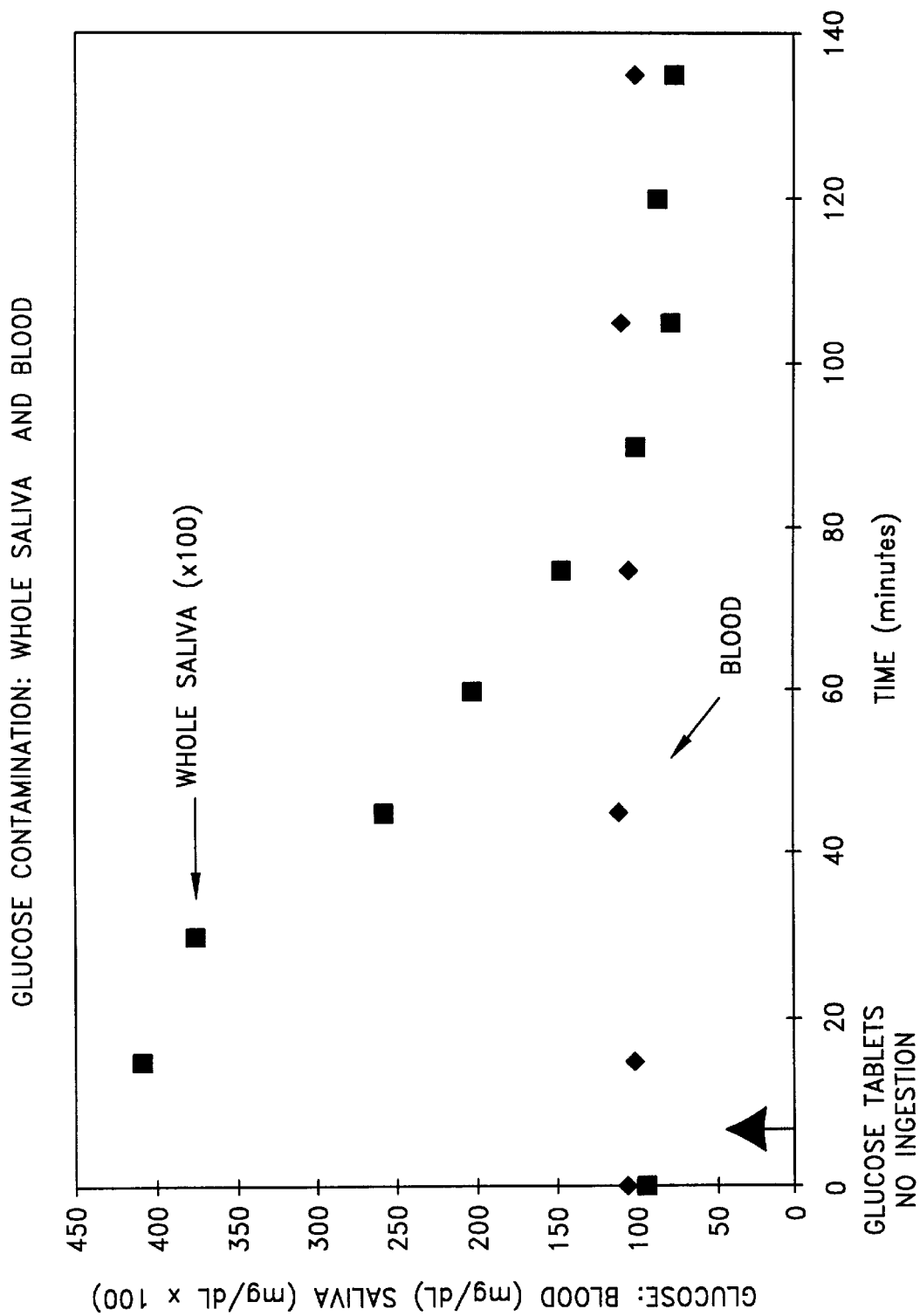

Two requirements of this noninvasive approach are that saliva glucose reflect blood glucose, and that the time lag in saliva be limited to minutes. The latter point is proven in the literature {Reuterving et al., 1987). The findings of Borg and Birkhed (1988) in which they showed a rise in saliva glucose following oral ingestion of glucose can be explained as an artifact of mucosal contamination which ostensibly duplicates the elevation in blood. The basis of the skepticism was that previous papers reported levels of saliva glucose that exceeded values observed and reported herein in subjects, even when blood glucose was relatively high. These are shown in FIG. 10A which illustrates the rise in saliva and blood glucose in one nondiabetic subject undergoing a modified Oral Glucose Tolerance Test, in which 50 g of glucose (in 200 mL $H_2O$)) was taken orally and whole saliva and blood (finger-stick) collected for assay of glucose at 15 minute intervals. This experiment did not use the present invention as shown in FIGS. 1 and 2 as it was necessary to sample frequently at intervals less than the device equilibration period. Both blood and saliva glucose rise in the early period. FIG. 10B shows a similar experiment done in the same individual. In this case, however; the subject rotated two 5 g glucose tablets within his mouth for four minutes, and next expectorated undissolved tablets and saliva, and rinsed mouth once with water prior to contributing whole saliva and blood samples. In this case, there was a transient elevation in saliva glucose as in the earlier experiment, but this one was not paralleled by blood glucose.

It is evident that glucose contamination of tissues of the mouth, especially when oral glucose load is high, can be the dominant source of glucose measured in saliva. The same contamination could apply when glucose loading is reduced to the content in an average meal. Table 6 shows that glucose collected in accordance with the present invention (referred to as "SalivaSac") tends to be higher in some individuals one to two hours after than immediately before lunch, even when blood concentrations increase only modestly between sampling periods.

TABLE 6

SalivaSac Glucose and Blood Glucose Before and After Lunch mg/dL

| Subject | Before Saliva | Before Blood | After Saliva | After Blood |
|---------|---------------|--------------|--------------|-------------|
| 1 | <0.12 | 77 | 1.22 | 103 |
| 2 | 0.18 | 89 | 5.13 | 98 |
| 3 | <0.12 | 102 | 1.38 | 107 |
| 4 | 0.43 | 101 | 1.49 | 103 |
| 5 | 0.17 | 98 | 0.51 | 132 |
| 6 | 0.49 | 96 | 1.64 | 142 |
| 7 | 1.32 | 100 | 0.26 | 74 |
| 8 | <0.12 | 82 | 0.46 | 92 |

SalivaSac ® in mouth for 20 minutes after citric acid stimulation; blood glucose measured using the same finger-stick strips and monitor (One-Touch ®). Meals unregulated for glucose content; after lunch samples taken 1–2 hour after meal. 0.12 mg/dL was the LOD (2 standard deviations criterion) in SalSac samples at the time this assay was done.

EXPERIMENT VI

As discussed above, the threshold for saliva glucose is a blood glucose of approximately 100 mg/dL or less. A study in hyperglycemic individuals in which whole saliva and glucose collected by the present invention were compared with blood glucose in finger-stick and venipuncture samples. These data are presented as evidence in support of the contention that the present invention is feasible when blood concentrations are normal to elevated. The entrance criteria for this study was a blood glucose of greater than or equal to 250 mg/dL. Subjects were not required to fast overnight, but were asked to refrain from eating for the three hours before samples were taken in mid-morning or mid-afternoon. Adult subjects meeting criteria placed a device made in accordance with the present invention in the mouth after stimulation with citric acid. The collection period was 20 minutes, after which subjects also donated whole saliva and venipuncture blood.

Figure 11A:
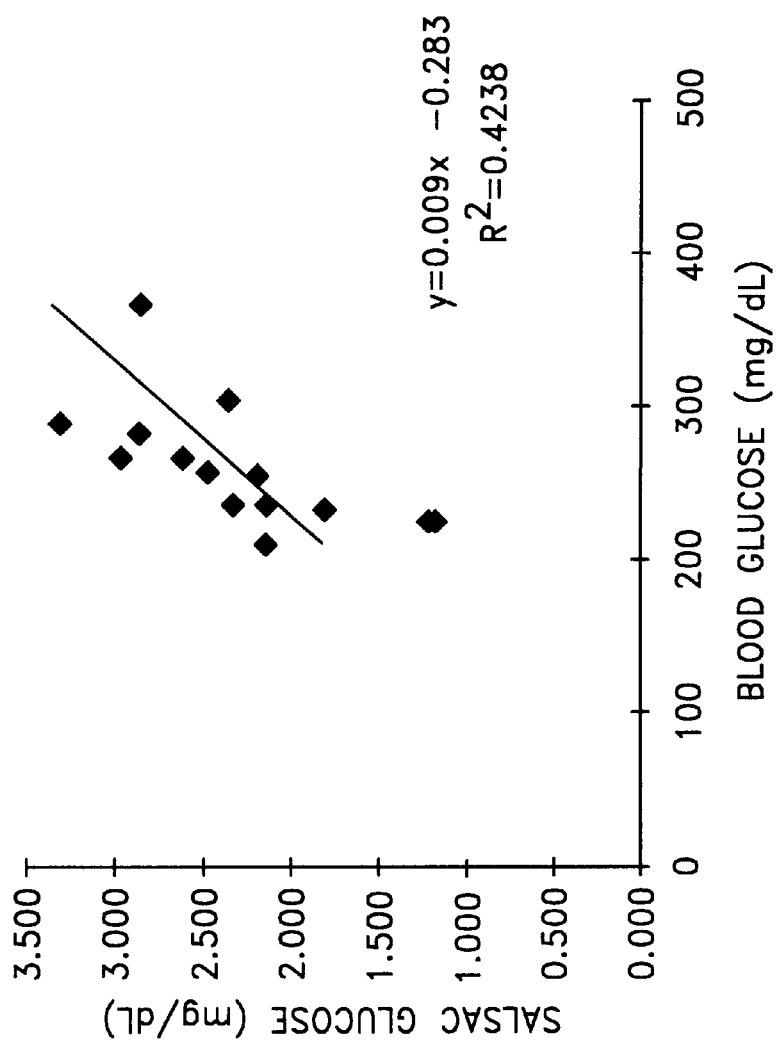
FIGS. 11A–C are graphs showing glucose collected by the present invention compared to finger stick glucose (A and C) and venipuncture (C) in hyperglycemic and normal subjects, FIG. 11A showing the results of 13 diabetic subjects, FIG. 11B showing a collection of data from subjects from the present study and an earlier study as described in the specification.

FIG. 11A shows glucose collected by the present invention plotted against finger stick glucose. Each subject used their own monitor to obtain the finger stick glucose value. SalivaSac and SalSac in the figures indicates use of the present invention. Variation in blood measurements by use of several monitors of unknown precision or calibration might have contributed to scatter in the correlation (Li et al., 1994). Nonetheless, there is a general correspondence between glucose and blood glucose. It is also evident that glucose collected by the present invention values in hyperglycemic subjects exceeded the typical concentrations observed in normoglycemic persons.

Figure 11B:
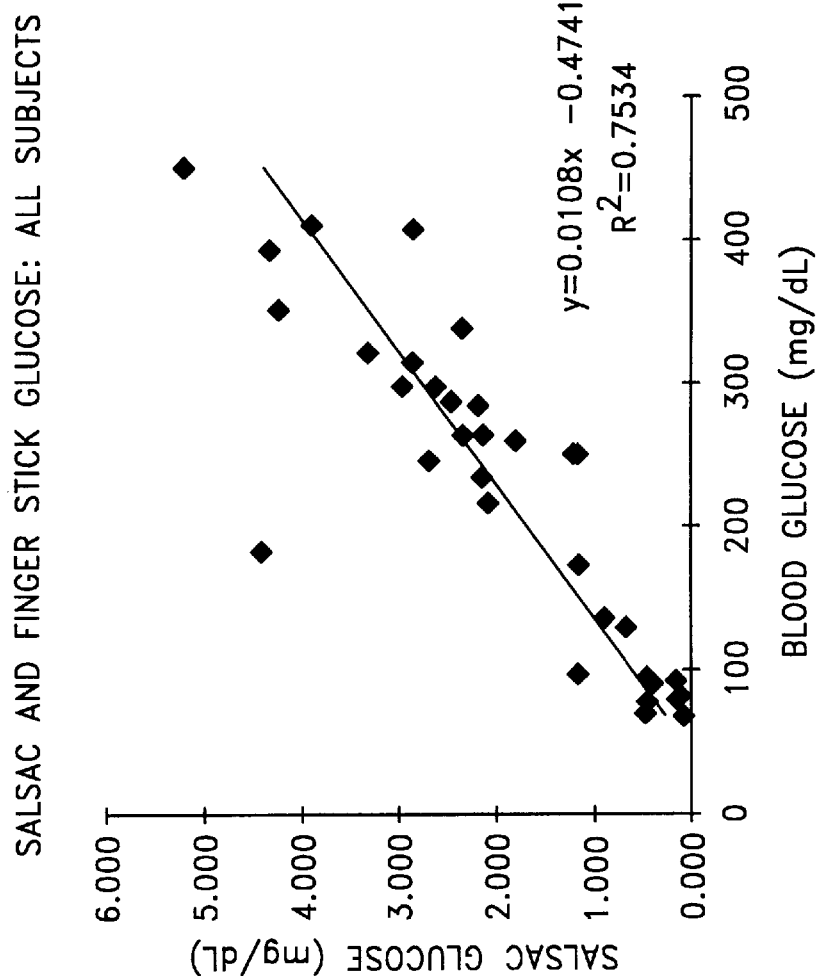
Figure 11C:
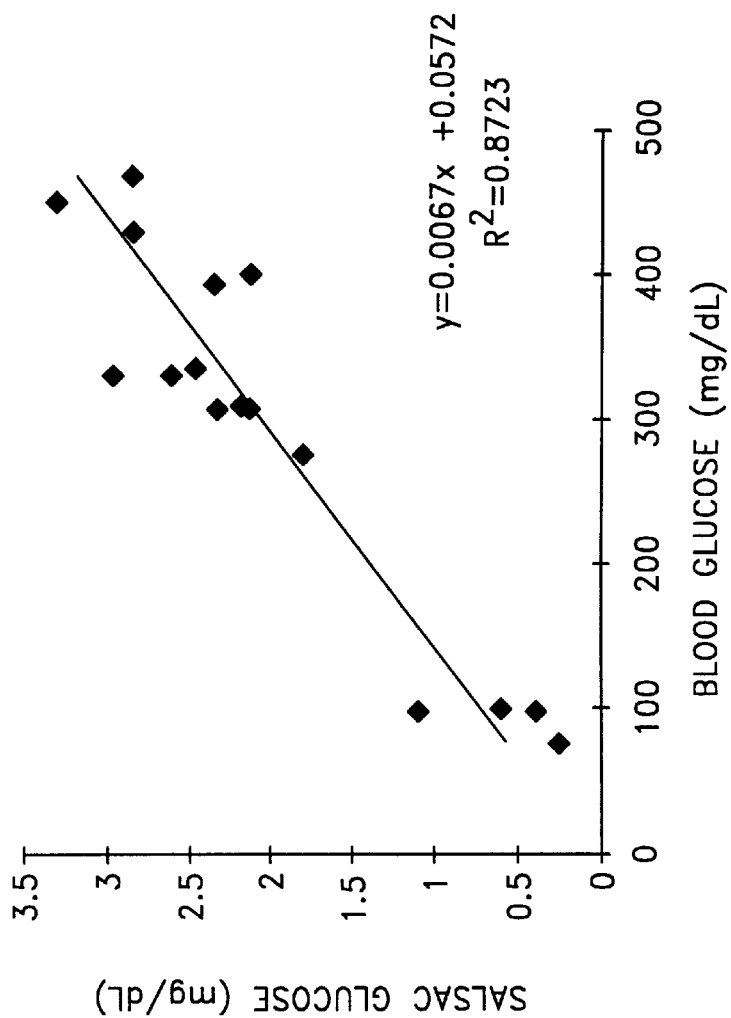

FIG. 11 combines the data obtained in the study of diabetics with data previously obtained using four nondiabetic and one diabetic subject. Each of the earlier subjects were sampled twice, once before lunch and once after, and both measurements are included in the figure.

Figure 12A:
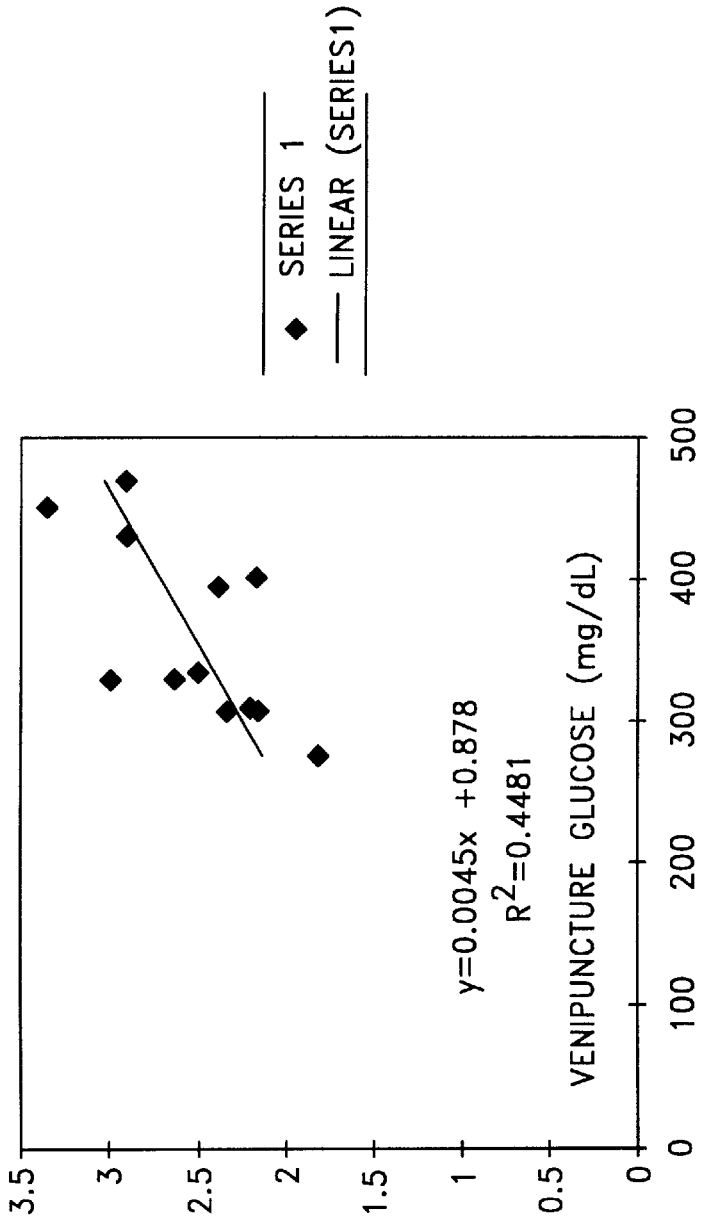
FIGS. 12A–B are graphs showing a correspondence between saliva glucose and venipuncture blood, FIG. 12A showing venipuncture vs. stimulated subject using the SalivaSac® (present invention) for collection of saliva.
Figure 12B:
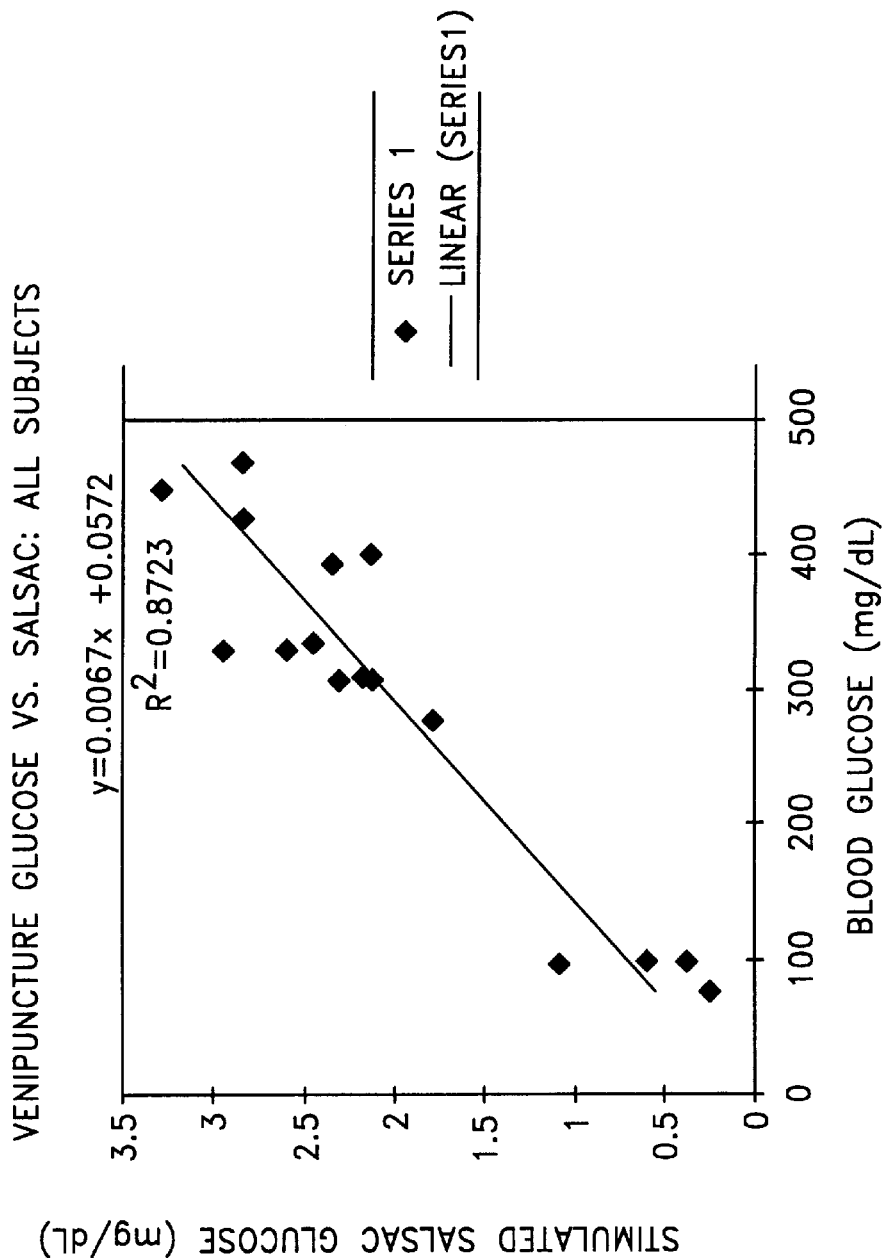

FIG. 12 presents data from the same experiment with diabetic and non-diabetic subjects. In this figure, the correlation between saliva glucose collected by the present invention and glucose in venipuncture blood measured by the reference method (Hexokinase; see above) is shown. When blood glucose exceeds approximately 70 mg/dL (in the normal range), there is a close parallel between blood and filtered saliva. Data on FIGS. 11 and 12 show that whether blood glucose is measured by the finger stick method (as is typical among diabetics) or by venipuncture (as occurs in medical practice), the present invention obtains a saliva sample that corresponds with the blood values. As noted above, the precise nature of the computation to estimate blood glucose has not yet been determined, though its general form is shown by the equations in FIGS. 11 and 12.

In view of the above, it can be concluded that glucose in saliva is quantitatively related to glucose concentration in plasma from which it is derived. The relationship is only effective to individuals and situations in which blood glucose is greater than 70–100 mg/dL.

Further, the above data demonstrate the feasibility and utility of the subject method wherein, generally, blood glucose is monitored by most generally, stimulating salivary glands secretion of saliva into oral fluid, collecting a sample of the oral fluid, detecting an amount of glucose in the sample and then quantitating blood glucose level based on the amount of glucose detected.

Throughout this application, various publication are referenced by authors and years. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of the description rather than of limitation.

Obviously, many modifications and variations of the present invention are possible in light of the above teachings. Therefore, it is to be understood that within the scope of the appended claims, reference numerals are numerals are merely for convenience and are not to be in any way limiting, the invention may be practiced otherwise than as specifically described.

REFERENCES CITED

BAUM, 1993, "Principles of saliva secretion", Acad. Sci, 694:17–23

BORG and BIRKHED, 1988, "Secretion of glucose in human paroitid saliva after carbohydrate intake", Scand. J Dent. Res., 96:551–556.

COHEN, 1988, "Non-enzymatic glycosylation proteins", Diabet. Ann., 4:469–484

LI, 1994, "Comparing self-monitoring blood glucose devices", Lab. Med., 25:585–590

REUTERVING et al., 1987, "Salivary flow rate and salivary glucose concentration in patients with diabetes mellitus", Diabet. Metab., 13:457–462.

SCHRAMM, April 1989, "Oral fluid collection article", U.S. Pat. No. 4,817,632

What is claimed is:

1. A noninvasive glucose monitoring device comprising:
   a housing comprising an outer membrane, an inner membrane, and a collection means for collecting a sample of the oral fluid;
   a stimulation means for stimulating salivary gland secretion of saliva into oral fluid, wherein said stimulation means is in said housing;
   detection means operatively connected to said collection means for detecting an amount of glucose in the sample; and
   quantitation means operatively connected to said detection means for quantitating blood glucose level based on the amount of glucose detected.

2. The noninvasive glucose monitoring device of claim 1 wherein said housing comprises a means of injection for dispensing said stimulation means therefrom and collection of oral fluid therein.

3. The noninvasive glucose monitoring device of claim 1 wherein said inner membrane is a dialysis membrane.

4. The noninvasive glucose monitoring device of claim 1 wherein said outer membrane is a filtering surface container defining an enclosed chamber.

5. The noninvasive glucose monitoring device of claim 1 wherein said housing contains osmotic means for drawing the oral fluid into said housing.

6. The noninvasive glucose monitoring device of claim 5, wherein said stimulating means stimulates salivary gland secretion and draws the oral fluid into said housing.

7. The noninvasive glucose monitoring device of claim 6, wherein said stimulating means is citric acid.

8. The noninvasive glucose monitoring device of claim 1 further comprises a support strip, comprising a first end and a second end, wherein said housing is mounted to said first end, said strip supporting said detection means and quantitation means therein and fluid transfer means for transferring oral fluid from said housing to said detection means and quantitation means.

9. The noninvasive glucose monitoring device of claim 8, wherein said housing further comprises a sealed membrane container and a piercing means for piercing an opening in said container to release the sample into said transfer means.

10. A noninvasive glucose monitoring device comprising:
    oral fluid collection means for collecting a sample of oral fluid comprising an inner membrane and an outer membrane, and
    blood glucose determining means for determining blood glucose level from the sample of oral fluid, wherein said determining means is operatively connected to said collection means.

11. A noninvasive fluid collection device comprising:
    oral fluid collection means for collecting a sample of oral fluid comprising an inner membrane and an outer membrane;
    a blood glucose determining means for determining blood glucose levels from the sample of oral fluid, wherein said determining means is operatively connected to said collection means; and
    saliva stimulating means for stimulating salivary gland secretion of glucose.

12. A noninvasive collection device comprising oral fluid collection means for collecting a sample of oral fluid comprising an inner membrane and an outer membrane, oral fluid dilution means for diluting the oral fluid to increase the rate of uptake of the oral fluid into said collection means and a blood glucose determining means for determining blood glucose levels from the sample of oral fluid, wherein said determining means is operatively connected to said collection means.

13. A method of monitoring blood glucose by:
    stimulating salivary gland secretion of saliva into oral fluid;
    collecting a sample of the oral fluid using a glucose monitoring device comprising an inner membrane and an outer membrane and a blood glucose determining means for determining blood glucose levels from the sample of oral fluid, wherein said determining means is operatively connected to said collection means;
    determining an amount of glucose in the sample; and
    quantitating a blood glucose level based on the amount of glucose detected.

14. The method of monitoring blood glucose of claim 13, wherein said collecting step is further defined as using a physical force to drive oral fluid through a filtering surface into a sample receptacle.

15. The method of monitoring blood glucose of claim 14, wherein the sample receptacle is a sealed, puncturable container.

16. The method of claim 15, wherein said method further comprises the further step of puncturing an opening in the receptacle to release the oral fluid collected therein, whereby a readable signal on a support strip indicative of the blood glucose level is produced.

17. The method of claim 14, wherein said physical force is an osmotic gradient, wherein said physical force osmotically drives the oral fluid into said sample receptacle.

18. A method of noninvasively monitoring blood glucose levels by collecting a sample of oral fluid using a glucose monitoring device comprising an inner membrane and an outer membrane and a blood glucose determining means operatively connected to a collection means for determining blood glucose levels from the sample of oral fluid and determining a blood glucose level therefrom.

19. A method of noninvasively collecting oral fluid by collecting a sample of oral fluid using a glucose monitoring device comprising an inner membrane and an outer membrane and a blood glucose determining means operatively connected to a collection means for determining blood glucose levels from the sample of oral fluid while stimulating saliva secretion.

20. A method of noninvasively collecting oral fluid by first diluting oral fluid to increase oral fluid uptake in a collection device and then collecting a sample of the oral fluid using a glucose monitoring device comprising an inner membrane and an outer membrane and a blood glucose determining means operatively connected to a collection means for determining blood glucose levels from the sample of oral fluid.

* * * * *